(12) United States Patent
Reichow et al.

(10) Patent No.: US 10,905,970 B2
(45) Date of Patent: Feb. 2, 2021

(54) SCENT BLENDING

(71) Applicant: Disney Enterprises, Inc., Burbank, CA (US)

(72) Inventors: Mark A. Reichow, Santa Clarita, CA (US); Samantha M. Catanzaro, Burbank, CA (US); David Lester, Los Angeles, CA (US); Steven A. Johnson, Pasadena, CA (US)

(73) Assignee: DISNEY ENTERPRISES, INC., Burbank, CA (US)

( * ) Notice: Subject to any disclaimer, the term of this patent is extended or adjusted under 35 U.S.C. 154(b) by 402 days.

(21) Appl. No.: 15/905,779

(22) Filed: Feb. 26, 2018

(65) Prior Publication Data

US 2019/0262739 A1    Aug. 29, 2019

(51) Int. Cl.

| | |
|---|---|
| *A61L 9/00* | (2006.01) |
| *A63J 5/00* | (2006.01) |
| *G05B 15/02* | (2006.01) |
| *A61L 9/12* | (2006.01) |
| *A63G 31/00* | (2006.01) |
| *A63J 25/00* | (2009.01) |
| *A61L 9/01* | (2006.01) |

(52) U.S. Cl.
CPC .   *A63J 5/00* (2013.01); *A61L 9/01* (2013.01); *A61L 9/125* (2013.01); *A63G 31/00* (2013.01); *A63J 25/00* (2013.01); *G05B 15/02* (2013.01); *A61L 2209/11* (2013.01); *A63J 2005/008* (2013.01)

(58) Field of Classification Search
CPC ... A61L 9/00; A61L 9/01; A61L 9/015; A61L 9/04; A61L 9/12; A61L 9/125; A61L 9/14; A61L 2209/133; A61L 2209/134
USPC ........................................................ 422/5, 305
See application file for complete search history.

(56) References Cited

U.S. PATENT DOCUMENTS

| | | | |
|---|---|---|---|
| 2,905,049 A | * 9/1959 | Laube | A61L 9/122 352/85 |
| 2007/0258849 A1 | * 11/2007 | Kent | A61L 9/035 422/5 |

* cited by examiner

*Primary Examiner* — Monzer R Chorbaji
(74) *Attorney, Agent, or Firm* — Dorsey & Whitney LLP

(57) ABSTRACT

One embodiment of the present disclosure may take the form of a method of dispersing scents in congruity with entertainment. Multiple scents are dispersed into the environment surrounding a participant at various points in congruity with visual entertainment. The scents are selectively provided at various times to coincide with the display of one or more elements in the entertainment experience such as a location or character. One embodiment of the present disclosure may take the form of a system for blending scents. The system includes an airflow source, a plurality of scent distributors, and a controller operably coupled to the airflow source and plurality of scent distributors to selectively control delivery of the scents from the plurality of scent distributors to bulk airflow delivered to a participant environment.

18 Claims, 8 Drawing Sheets

SCENT BLENDING

FIELD

The present disclosure relates generally to scent delivery and entertainment methods and systems.

BACKGROUND

Scents can induce olfaction and olfaction memory in the brain of a subject. Scents are processed by the olfactory bulb, which extends from the nose to the bottom of the brain. The olfactory bulb is an integral part of the limbic system which is the same part of the brain that performs functions including long-term memory, motivation, behavior, and emotion. Such close coupling may be why the sense of smell triggers memories and emotions for most people. Scent is arguably the most powerful human sense as it is the only sense integrally processed in the limbic system along with other fundamental functions such memory and emotion. Scents can be used to trigger memories or emotional responses.

The science of scent augmentation likely began historically as a way to mask or cover unpleasant smells that occurred in an environment. Perfumes and plant extracts were used to cover offensive odors from people and animals. Even today scent augmentation has been used at large scale malodorous facilities such as the Blue Plains wastewater treatment facility that notoriously causes unpleasant odors in Alexandria, Va. This history focused on using scent to hide or overpower scents in an environment and was in direct contrast with the idea of using scent augmentation artistically to recreate an environment for entertainment purposes.

It is useful to think about scent experiences by way of analogy to audio sensory experiences. Single audio tones can be heard and can convey information, but they can be unpleasant to listen to and distracting. This is even more true when the volume is poorly controlled. In contrast, music produced by an orchestra comprises a complex and rich combination of component sounds with individual volumes and notes varying over time to produce a nuanced and enjoyable audio experience. In a similar way, scents we experience in our natural world comprise a rich and nuanced combination of scents generated by multiple sources, combining in different ways over time to allow us to perceive an olfactory scene with interest and enjoyment.

Although media-based entertainment has evolved rapidly to provide higher resolution audio and video, wider gamut and dynamic range, for example, use of scent in entertainment has evolved little if at all. Previous attempts to trigger these emotional responses for the purpose of creating a deeper immersive experience have been primitive and essentially monotonic and binary, as they typically involved an intense distribution of a single scent, on/off, then another on/off. Accordingly, the detectable scent is often not distributed and synced realistically to the visuals or of a quality to cause believable connections to the entertainment with audience members. Thus, the detectable scent often distracted from an entertainment experience by drawing attention away from a story to the scent itself. Scent distribution was a crude caricature of what might be happening on a movie screen rather than an active contributor to the subtle and complex nuances presented by high definition imagery and audio.

SUMMARY

One embodiment of the present disclosure is a method for providing time-varying scent effects in a scripted entertainment event. The method includes providing a scent score defining a sequence of scent dispersion instructions arranged on a timeline. The method includes executing the sequence of scent dispersion instructions using one or more scent dispersion devices to produce multiple scents having intensity and composition that vary over time according to the scent score. The method includes distributing multiple scents produced by the one or more scent dispersion devices to a participant in the entertainment event, where each scent dispersion instruction of the sequence of scent dispersion instructions corresponds to at least one of the multiple scents and is distributed to the participant in time with a story element of a corresponding story script for the scripted entertainment event.

One embodiment of the present disclosure is a method of dispersing the scents in congruity with entertainment. The method includes providing a first scent media producing a first scent representing a first set of physical objects appearing in the entertainment. The method includes displaying an entertainment experience comprising time-varying representations of the first set of represented physical objects. The method includes, while displaying the entertainment experience, controlling a quantity of scent molecules from the first scent media introduced into air surrounding a participant in coordination to a characteristic of the time-varying representations, wherein the characteristic includes a perceived distance between the participant and the first set of represented physical objects, a perceived size of the first set of represented physical objects, a perceived density of the first set of represented physical objects, a perceived atmospheric conditions between the participant and the first set of represented physical objects, or perceived obstructions between the participant and the first set of represented physical objects.

One embodiment of the present disclosure is a method of dispersing scents in congruity with story-based entertainment. The method includes providing a first scent associated with a first story element, providing a second scent associated with a second story element, and while displaying the story-based entertainment, controllably releasing the first and second scents in congruity with at least one of the first or second story elements.

One embodiment of the present disclosure is a method of dispersing scents in congruity with entertainment. The method includes dispersing a first scent in a perceivable magnitude into a breathing air volume of a participant during a first time period for a first duration and reducing the perceivable magnitude of the first scent during a second time period for a second duration.

An embodiment of the disclosure includes a scent blending system. The scent blending system includes an airflow source that generates a bulk airflow; a plurality of scent distributors fluidly connected to the bulk airflow, wherein each scent distributor corresponds to a scent; and a controller in electrical communication with the scent distributors, wherein the controller selectively activates the scent distributors to add one or more scents to the bulk airflow

SPECIFICATION

Overview

Figure 1A:
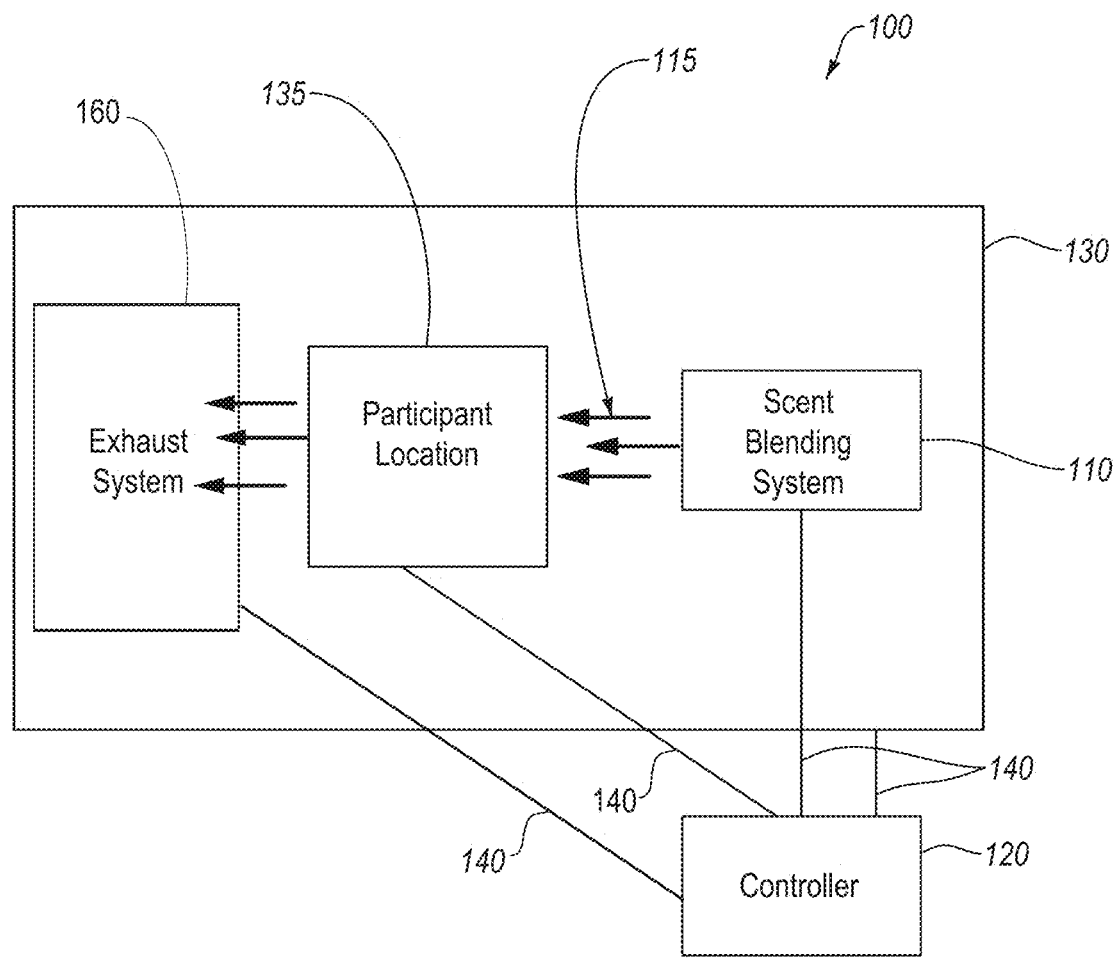
FIG. 1A is a system diagram illustrating a scent dispersing system in an entertainment environment.

The present disclosure is related to systems for dispersing scent(s) in concert with non-scent entertainment and methods for dispersing scent(s) in concert with non-scent entertainment, such as a still and video display, motion picture, amusement park ride, augmented and virtual reality experiences, theatrical performances, sporting events, etc., and generally any type of experience where scent can augment the entertainment. Unlike conventional scent augmentation systems and methods that try to overpower and replace unpleasant odors, this disclosure describes methods and systems for artistically delivering scent in a manner that creates a representation of a physical space and physical objects that are represented in the entertainment experience. Moreover, systems and methods described herein enable nuanced scent delivery and blending with fidelity that compares to that of visual, auditory, and tactile components of entertainment experiences.

One important feature of the present disclosure is the development of a scent palette that cooperates with an entertainment experience. In nature every object and surface has some scent such that natural environments are a complex interaction of scents that vary over time with far too many components to reproduce. The scent palette is an implementation-specific set of scents that when dispersed and blended in a controlled manner are sufficient to stimulate the olfactory functions of participants in the experience. This stimulation may result in conscious or subconscious perception of the scent and may trigger formation of memories, recollection of memories, and various emotional responses in the participants. Scent palette creation is an artistic endeavor of identifying important objects in a scene of an entertainment experience, determining scents for those objects, identifying dispensable scent molecules that recreate the determined scents. Each of these steps reduce the size of the scent palette. The scent palette is further reduced by considering interaction between scents in various scenes of the entertainment experience. In some cases scents may be removed from the palette when they conflict or clash with scents from other scenes, or may be removed for practical purposes if they appear in very few scenes. The general flow described herein results in an artistically influenced scent palette containing a set of scents that alone and in mixtures enable the smells of a particular scene to be recreated in a controlled fashion in concert with other non-scent components of the entertainment experience.

The scent dispersing systems disperse a plurality of scents into the environment proximate a participant (e.g., audience member, spectator, guest, user, or rider) in congruity with one or more non-scent components (e.g., visual, audio, or haptic stimuli) of an entertainment experience (e.g., a film, amusement park ride, play, etc.). The systems can be used to associate or deliver one or more scents with one or more story or represented physical elements of the entertainment. For example, a first scent is emitted in association with display of a first element (e.g., a first character, location, prop or represented physical object, or type of action) of the entertainment and a second scent is emitted in association with display of a second element (e.g., a second character, location, prop or represented physical object, or type of action) of the entertainment such that a participant may associate the first scent with the first element(s) and the second scent with the second element(s). The first element and the second element may correspond to locations or story elements in the entertainment. The systems and methods can also emit the scents in proportion to an apparent (e.g., represented) or participant-perceived proximity to, or focus on, the first element or the second element present in the entertainment. As an example, consider a scene in which a participant is in a parking lot of a diner. Initially a mixture of parking lot scents (e.g., fuel, exhaust, perhaps wet pavement) are mixed with diner scents (e.g., warm food, coffee, oil aerosol). As the participant approaches the diner the scent mix can be altered continuously to increase the diner scents and decrease the parking lot scents both to create the experience of becoming closer and to encourage focus on the diner rather than the parking lot. Similarly, when an action occurs such as opening the front door of the diner, the diner scent(s) intensity can be increased further as the obstruction of the door is removed and the parking lot experience fades away.

The amount of the first scent or one or more additional scents can be selectively emitted to achieve an olfactory response associated with one or more elements of the entertainment experience. The scents can be mixed in order to evoke an olfactory transition from one element to another element in the entertainment. The olfactory transition may heighten the entertainment experience, such as immersing a participant in an environment displayed on a screen or surrounding a participant position (such as on a ride) and transitioning the senses of the participant from element to element (e.g., displayed first location to displayed second location). Particularly when a scent palette enables the distribution of diegetic scents—scents that appear to come from sources (e.g., props, and objects) that are visually, audibly, and/or tactilely represented in a scene—it is believed that the perception of immersion is greatly enhanced because the participant smells just what a character in the scene would smell.

In some instances, the dispersion and blending of scents is congruous with the depiction or focus on various elements of the entertainment. For example, scents are blended and transitioned from an olfactory background to an olfactory foreground of the entertainment experience based on the location of elements associated therewith in the entertainment or the location of the participant in the entertainment, e.g., as a character walks closer to a location, the scent associated with that location increases correspondingly. For example, when the scent transitions are paired with visual and sound transitions from parking lot scenes and sounds to diner scenes and sounds, the participant experiences a greater immersion into the entertainment. Such scent transitions can provide a sense of changing size of a scent source in congruity with the visual and audio representation of a growing object, such as a growing beanstalk or peach; a sense of changing location, depth, or amount of scent source(s) in congruity with the visual and audio representation such as upon entering donut shop or entering a field of flowers; or a sense of changing conditions of a scent source, such as changing weather conditions (e.g., fog, wind) or a scent source withering.

In some embodiments, a scent delivery system is used to tailor the scent delivery to a participant. The scent delivery system includes an airflow source, a controller, and one or more scent distributors. The airflow source and scent distributors are activated to deliver concentrated scent into a bulk (e.g., generic) airflow stream, which is then driven around and/or past a participant's nose. The systems can be positioned within an entertainment environment, such as an amusement park ride, a theater, one or more display screens, a stage, etc. The controller can synchronize the release of the scents with the entertainment (e.g., scenes in a film) provided in the entertainment environment, as well as control bulk airflow from the airflow source to induce a sensation of wind or movement.

The scents can be delivered to the bulk airflow and participant continuously, by nebulizing, evaporating, atomizing, opening valves, providing pressurized air, etc. The amount of scents added to the bulk airflow can be selectively controlled to provide a selected magnitude of the scent(s) perceived by the participant. The scents may be added to the bulk airflow via one or more pulses of individual scents where the length or magnitude of the pulses can be changed to modify the participant experience. For example, pulses of a first scent can be provided in a greater amount and/or duration as the entertainment draws a participant's attention to a first element (e.g., film enters a first setting or a ride enters a first location) and can be reduced as the entertainment draws the participant's attention to a second element (e.g., film enters a second setting, an additional element enters the first setting, ride moves to a second setting, etc.). As the pulses of the first scent are reduced, pulses of a second scent may be increased in amount and/or duration to evoke the olfactory sensation of a transition from entertainment element to entertainment element as the entertainment draws the participant's focus to a second element. Accordingly, the scents can be provided in various proportions and can be mixed to provide transitions from one scent to another in congruity with (e.g., in conjunction with, in combination with, or in concert with) changes or movement in the entertainment or to provide a new scent resulting from the combination of the first scent and the one or more additional scents.

Scents can be added to the environment of an amusement park ride rider to provide olfactory transitions which heighten the entertainment experience. For example, a rider can sit in a ride seat that is selectively movable and has a scent distribution system positioned in front of the rider. The amusement park ride can be a first person visual experience where the seat is moved in congruity with a visual, auditory, and haptic depiction of movement on one or more displays. The scent distribution system can speed up and slow down airflow across the rider and can selectively distribute a plurality of scents into the environment around the rider in congruity with visual depictions of settings, items, characters, movement, or other elements in the display(s) of the ride. For example, the seat can be made to appear like the seat of a biplane and the ride may depict flying the biplane over an ocean when the scent distribution system disperses a fresh air scent and a water scent into the bulk airflow that passes over the participant. The ride can depict the biplane diving, the seat can tilt, and the bulk airflow can speed up to induce the sensation of diving. The amount of scents dispersed into the bulk airflow can be reduced while the dive is depicted because the rider may hold their breath or be focused on other senses during the dive. As the biplane approaches the ocean during or after the dive, the proportion of the water scent is increased with respect to the proportion of fresh air scent to evoke the sensation of proximity to the water. Accordingly, the scent distribution system heightens the sensory experience of the amusement park ride.

DETAILED DESCRIPTION

FIG. 1A illustrates a scent dispersing system 100 in an entertainment environment including a scent blending system 110, a controller 120 coupled to the scent blending system, and an entertainment environment 130 (or portions thereof, such as a projector or rider seat) operably coupled to the controller 120 and associated with the scent blending system 110. The controller 120 selectively and synchronously controls the delivery of one or more scents into the entertainment environment 130 from the scent blending system 110. For example, the controller 120 delivers two different scents into the entertainment environment 130. The controller 120 may include a computer, tablet computer, or other electronic device as described in more detail with respect to FIG. 6. For example, the controller 120 can be a computer in communication with one or more devices within the entertainment environment, such that the controller can synchronize delivery of the scents with selected portions of the entertainment, such as displayed locations, characters, etc.

The entertainment environment 130 may be a stage, an amusement park ride, or the like. Often, the entertainment environment 130 will include one or more stages, screens, monitors, displays, projectors, animatronics, or other visual components. In embodiments, the entertainment environment 130 includes audio and haptic components, such as audio speakers, ride seats, and vibration sources. A participant or user may be free to roam within the entertainment environment, or in some instances may be located at a participant position 135, such as a seat or other predefined or known location in the entertainment experience, such as a theater seat, an amusement park ride seat, or any other site configured to accommodate a participant during an entertainment experience.

The scent blending system 110 is positioned to provide the plurality of scents to the region of participant position 135. For example, the scent blending system 110 may be positioned in front of the participant position 135 such that the emitted scents are delivered to a participant located in the participant position 135. The scent blending system 110 can be configured to emit scents to a single individual, such as through a personalized delivery or may be oriented and positioned to emit scents to two or more individuals. For example, each participant position 135 may include a scent blending module to allow direct delivery of the scents to a participant or a single scent blending module may be used to delivery to a participant group (e.g., multiple seats) or the entire entertainment environment. In instances where each participant has his or her own scent blending module, the scent experience may be enhanced, as well as personalized for particular participants.

The scent blending system 110 generally includes an airflow source that delivers a bulk airflow 115 to a delivery location, such as the participant or user position. The plurality of scents are introduced into the bulk airflow 115 and then travel therewith to each the participant(s). The bulk airflow 115 may be increased or decreased (by the controller 120) in congruity with one or more aspects of the entertainment experience. For example, the bulk airflow 115 may be increased to evoke a sensation of acceleration, velocity, or presence in a windy location. As bulk airflow is increased, the amount of scents may be increased to ensure a participant perceives the scents passing by in the airflow. Similarly, the bulk airflow may be decreased and the delivery of the scents may be decreased or increased to maintain or increase the scent experience. In some embodiments, the amount of emitted scents is decreased as the bulk airflow is increased, in order to conserve scent media when a participant's attention may be focused on senses other than smell.

In embodiments, the scent blending system 110 includes an exhaust system 145 operably coupled to the entertainment environment 130. The exhaust system 145 includes one or more exhaust fans, ducts, or other components to remove a volume of air from a space at a selected rate. For example, the bulk airflow 115 may be removed from the entertainment environment 130 at a selected rate by controlling one or more exhaust fans (not shown) of the exhaust system 145 to operate at a selected rate. By selectively controlling the speed, duration, and timing of operation of the exhaust system 145, the scent dispersion system 100 may present a plurality of scent(s) without causing unwanted mixing (e.g., cross-contamination) of subsequently presented scents. For example, when a plurality of scents are mixed to transition from one scent combination to another scent combination, the controller 120 can increase the speed of the exhaust system 145 as the scents are transitioned to a second scent mix to remove more air and scent from the entertainment environment to prevent or reduce saturation of the first scent mix in the entertainment environment when the second scent mix should be the predominate scent presented to the participant. In embodiments, the exhaust system 145 includes one or more scrubbers to remove scents from the bulk airflow and ducts to return the clean air back to the bulk airflow source or into the entertainment environment without the scents.

The controller 120 may be operably coupled to one or more devices in the entertainment environment 130 (e.g., screen, amusement park ride, participant position 135, exhaust system 145, etc.) and the scent blending system 110 via one or more connections 140. The one or more connections 140 are wireless connections or hardwired connections. In embodiments, the one or more connections 140 transmit electrical power or data between components of the system 100. For example, the controller 120 may send actuation signals to the scent blending system 110 responsive to a currently displayed scene in the entertainment displayed in the entertainment environment. Responsive to the actuation signals, the scent blending system 110 may provide a plurality of scents to the entertainment environment in synchronization with entertainment controlled by the controller 120. In embodiments, such control is based on a common time scheme monitored or co-initiated by the controller 120. Aspects of the scent blending system 110 are described in more detail below.

Figure 1B:
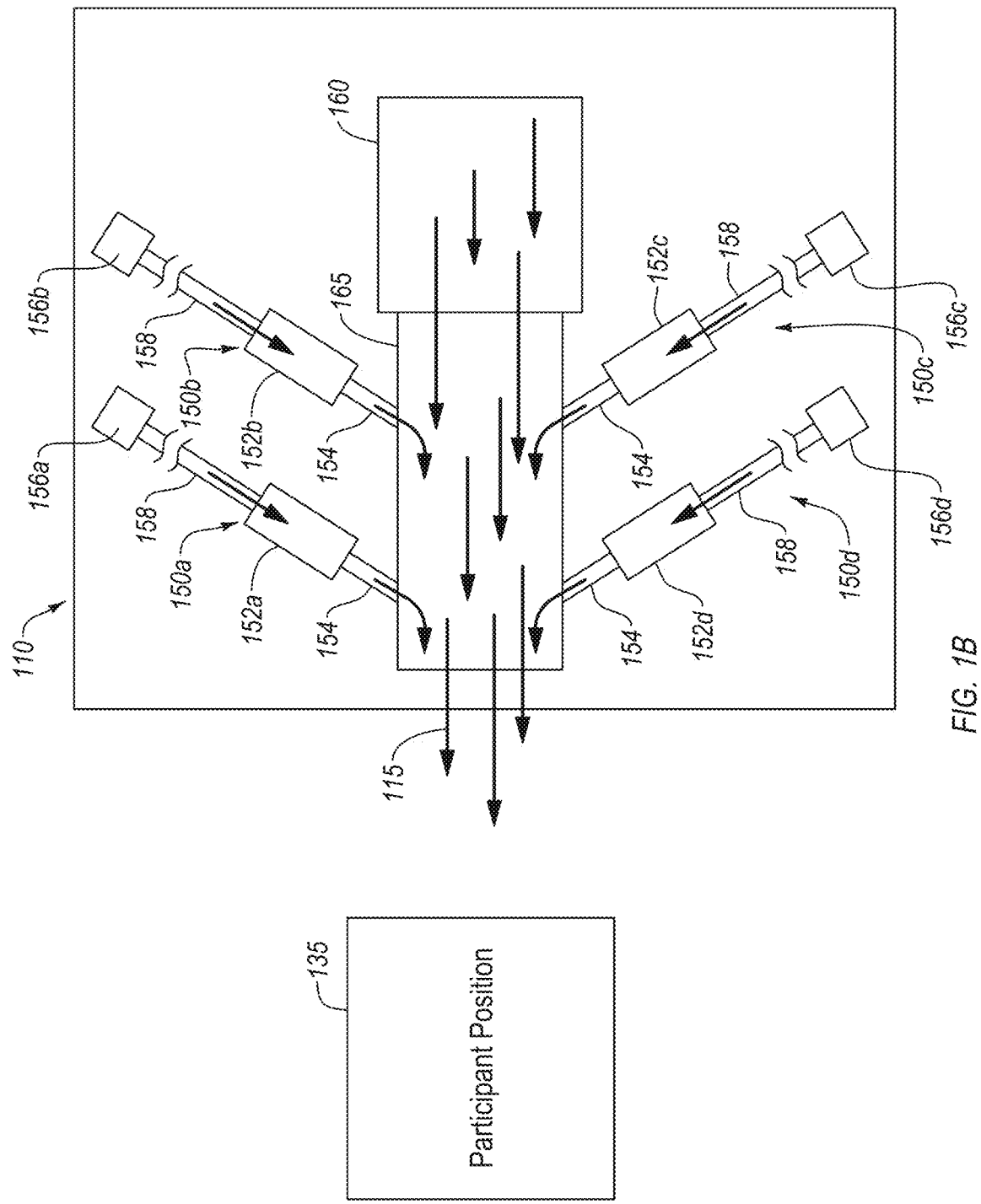
FIG. 1B is a system diagram of a portion of the scent dispersing system of FIG. 1A.

FIG. 1B is an example of a scent blending system 110 of FIG. 1. In this example, the scent blending system 110 includes an airflow source 160 to generate a bulk airflow 115, a bulk airflow conduit 165 to direct the bulk airflow 115, a plurality of scent distributors 150a-150d in fluid communication with the bulk airflow 115 in the entertainment environment, and the controller 120 (FIG. 1). In embodiments, the bulk airflow 115 generated by the bulk airflow source 160 is directed to the participant in the participant position 135 through the bulk airflow conduit 165. In embodiments, the bulk airflow source 160 is a fan, a turbine, or compressed air source. The scents from the scent distributors 150a-150d are added to the bulk airflow 115 and delivered to the participant in the participant position 135. In embodiments, each component of the scent blending system 110 is contained in a common housing or body. In some embodiments, some components of the scent blending system 110 are contained in a common housing or body. For example, the airflow source 160 can be housed in a location remote from the other components of the scent blending system 110 and the bulk airflow conduit 165 extends between the locations.

Each of the scent distributors 150a-150d individually and controllably provide a respective scent to the bulk airflow 115 and to that end each scent distributor 150a, 150b, 150c, and 150d includes a respective scent source 152a, 152b, 152c, or 152d. The scent sources 152a, 152b, 152c, and 152d may contain a first scent, a second scent, a third scent, and a fourth scent, respectively. In one embodiment, the scent sources 152a, 152b, 152c, and 152d are canisters containing a scent media, such as a scent-soaked media or scented oil, where each canister contains a different scent and scent media. For example, the scent media may include scent-soaked beads (e.g., essential oil-soaked beads). In other embodiments, the scent sources 152a, 152b, 152c, and 152d may each include a canister containing a scent atomizer such as a fluid atomizer, where each canister contains a uniquely scented fluid (e.g., scent media). In embodiments, a plurality of conduits 154 fluidly couple and direct the scent distributors 150a-150d (e.g., scent sources 152a-152d) with the bulk airflow 115. This allows the scent distributors 150a-150d to individually or collectively provide a selected amount of scent(s) to the entertainment environment from the scent sources 152a-152d. While shown as being located in an intermediate portion of the bulk airflow conduit 165 and sequentially distributed, in examples, each of the conduits 154 are located at the same longitudinal point of the bulk airflow conduit 165 or at an exit of the bulk airflow conduit 165. For example, in a longitudinal bulk airflow 115, each conduit 154 can be located laterally across the same longitudinal point in the bulk airflow 115. In such examples, the even alignment of the conduits 154 in the bulk airflow 115 prevents pollution of the bulk airflow 115 by downstream conduits 154. In examples, where the conduits 154 are aligned at an exit of the bulk airflow conduit 165 the position of the conduits 154 (e.g., outlets of scent distributors 150a-150d) prevents pollution of the bulk airflow conduit 165 with the scents. Each of the scent distributors 150a-150d is electrically coupled to the controller 120. The controller 120 selectively activates the scent distributors 150a-150d add one or more scents to the bulk airflow.

Each of the scent distributors 150a-150d may be fluidly coupled to an air source 156a-156d, respectively. The air sources 156a-156d provide pulses of air to and through the scent sources 152a, 152b, 152c, and 152d, respectively, which propels discrete volumes of the respective scent(s) to the bulk airflow 115. The one or more pulses may atomize at least some of the scent(s) in the scent sources 152a-152d and force the atomized scents into the bulk airflow 115. In embodiments, the air sources 156a-156d may include one or more of a compressed air source, a blown air source, or one or more valves. In embodiments, a solenoid valve is connected to each scent distributor 150a-150d, such as between at least one of the scent source 152a-152d and the air source 156a-156d or the scent source 152a-152d and the bulk airflow 115. The solenoid valves can be selectively actuated to control the delivery of the scents from the scent sources 156a-156d.

In embodiments, the air sources 156a-156d are individual compressed air sources such as compressed gas tanks each individually controllable (by the controller 120) to selectively emit scent into the bulk airflow 115. In embodiments, conduits 158 fluidly couple the scent sources 152a-152d to the air sources 156a-156d. In embodiments, the air sources 156a-156d are a single compressed air source and conduits 158 fluidly couple the scent sources 152a-152d to the single compressed air source. In such embodiments, a plurality of valves (not shown) are disposed between the scent sources 152a-152d and the single compressed air source. Controlled actuation of the solenoid valves (e.g., by the controller 120) pulses the scent(s) into the bulk airflow 115. Accordingly, the scent distributors 150a-150d are individually controllable to provide a selected amount of scent(s) to the entertainment environment from the scent sources 152a-152d.

Referring to both FIGS. 1A and 1B, the controller 120 is operably coupled to one or more of the scent distributors 150a-150d (e.g., air sources 156a-156d), the exhaust system 145, and the bulk airflow source 160. The controller 120 can be operably coupled to devices or a controller of the devices in the entertainment environment 130 to synchronize release of scents with aspects of the entertainment, such as movements, displays, etc. The controller 120 controls one or more of bulk airflow (e.g., air speed), amount and duration application of scent(s), removal of a volume of air from the entertainment environment, and the entertainment environment (e.g., film, tilt or speed of participant position, etc.). For example, the controller 120 selectively controls the plurality of scent distributors 150a-150d (e.g., air sources 156a-156d) to introduce scent(s) to the bulk airflow 115. The controller 120 selectively controls the delivery and mixing of multiple scents or the tapering-off of one scent in congruity with the tapering-on of at least a second scent. The controller 120 selectively controls how fast the bulk airflow travels in the entertainment environment and transitions between one or more bulk airflow speeds. The bulk airflow speeds can be 0 mph or more, such as 0 mph to 40 mph, 1 mph to 20 mph, 20 mph to 40 mph, 40 mph to 60 mph, or less than 40 mph. Transitions between any of the bulk airflow speeds may be carried out over a selected duration, such as going from 0 mph to 40 mph in less than 5 seconds. The controller 120 selectively controls how fast a volume of air containing the scent(s) is removed from the entertainment environment such that additional scents may can be presented on a clean palette (e.g., without pollution of prior or unwanted scents).

In addition to changing the scent delivery and distribution, the controller 120 can change the orientation and location of the participant, as well as environmental experiences. For example, the controller can vary an angle of tilt of a participant position in congruity with an increase in bulk airflow speed to evoke the sensation of falling or flying. In another example, the controller 120 drives the display of one or more images on a display in connection with the scent distribution. In embodiments, the entertainment experience includes portions where the participant's focus is directed to an entertainment component other than scent(s) and the controller 120 may increase or decrease the amount of scent(s) applied to the bulk flow accordingly, such as in order to provide stronger, more noticeable amounts of scent(s) or to conserve the scent(s) until a participant's attention may be more readily directed to the scent(s).

In embodiments, the controller 120 causes the plurality of scent distributors 150a-150d to add the one or more scents to the bulk airflow in one or more pulses, such as via activation of solenoids in the scent distributers that are in electrical communication with the controller 120 or activation of air sources 156a-156d. The solenoid valves can be electrically coupled to the controller 120 which selectively opens the solenoid valves to release one or more pulses air into the scent sources 152a-152d and/or scent into the bulk airflow 115. For example, electrical signals are sent from the controller 120 to the solenoids according to a timed program (e.g., scent score) to selectively open the solenoids to emit scents according to a schedule. The controller 120 selectively controls a duration and/or pressure (e.g., magnitude) of air pulses from the air sources 156a-156b through one or more of the scent sources 152a-152d to cause a selected amount (e.g., volume) of atomized scent molecules to enter the bulk airflow 115.

In embodiments, the controller 120 selectively controls the plurality of scent distributors 150a-150d to add one or more scents to the bulk airflow according to a time scheme, such as a common time code, clock, or timer. The controller 120 uses the common time scheme to synchronize the entertainment experience, such as one or more of a tilt, movement, or position of the participant position or the display of a images (e.g., film) on a display screen with delivery of scents.

While shown as being operably coupled to the bulk airflow 115 via conduits 154, in some embodiments, scent sources 152a, 152b, 152c, or 152d are directly coupled to the bulk airflow 115. For example, the scent sources 152a-152d can be mounted directly onto (e.g., on an output orifice) or into the bulk airflow conduit 165 without the conduits 154 therebetween. Any number of scent distributors and associated scent sources can be included in a scent dispersing system, such as at least 2, 3, 4, 5, 6, 7, 8, 9, 10, or 20 scent distributors, or ranges between any combination of the foregoing.

The systems herein selectively deliver a plurality of scents in congruity with an entertainment experience. The plurality of scents can be combined, blended, or transitioned from one scent to another. For example, a first scent can be emitted while an amusement park ride is at or displaying a first location, and congruous (e.g., in concert or contemporaneous) with a move to a second location, the first scent is tapered off while a second scent is ramped on (where at least some of the first and second scents are emitted congruously (e.g., in concert with each other) to provide an olfactory transition between locations). The delivery of the plurality of scents may heighten the participant's experience during display of an entertainment experience, by providing a non-visual means of associating locations or other story elements. For example, during an amusement park ride, scent(s) provided in congruity with the location(s) of the participant position during the progress of the ride provide an olfactory indication of a transition from one scene or location to another scene or location in the ride. In embodiments, at least two of the plurality of scents are congruously emitted to combine and provide a new scent from the mixture of scents. The system 100 may be used to deliver the scents in a selected fashion, such as according to any of the methods below.

Figure 2:
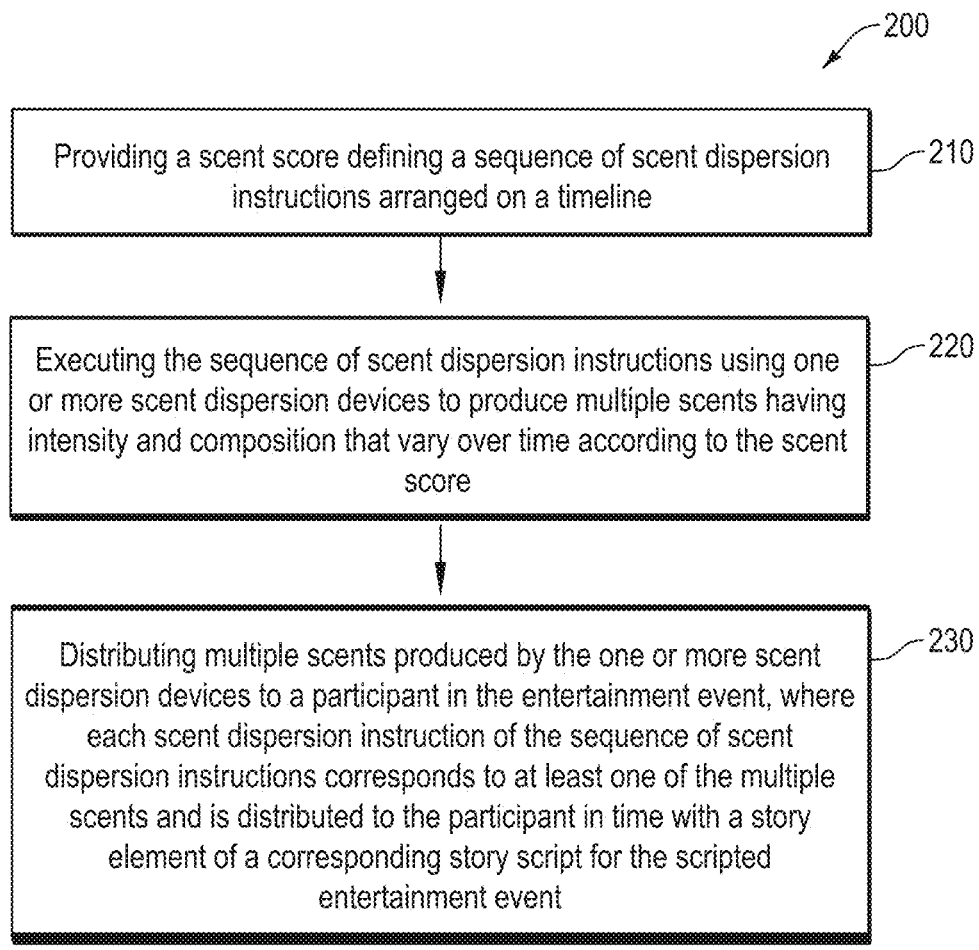
FIG. 2 is a flow diagram of a method for providing time-varying scent effects in a scripted entertainment event.

FIG. 2 is a flow diagram of a method 200 for providing time-varying scent effects in a scripted entertainment event. The method 200 includes the act 210 of providing a scent score defining a sequence of scent dispersion instructions arranged on a timeline; the act 220 of executing the sequence of scent dispersion instructions using one or more scent dispersion devices to produce multiple scents having intensity and composition that vary over time according to the scent score; and the act 230 of distributing multiple scents produced by the one or more scent dispersion devices to a participant in the entertainment event, where each scent dispersion instruction of the sequence of scent dispersion instructions corresponds to at least one of the multiple scents and is distributed to the participant in time with a story element of a corresponding story script for the scripted entertainment event. In embodiments, additional acts may be performed in addition to or in place of the acts 210-230.

The act 210 of providing a scent score defining a sequence of scent dispersion instructions arranged on a timeline includes providing the scent score in digital format. For example, providing a scent score defining a sequence of scent dispersion instructions arranged on a timeline includes providing the scent score via a computer or controller. The scent score includes a sequence of instructions for controllably actuating or modulating the scent distributors (FIG. 1B) to deliver scent(s) to the bulk airflow at selected times in the scent score timeline. The selected times may be in congruity with represented movement of the participant, represented movement of objects (e.g., characters, physical objects, etc.) in the entertainment, movements of the participant, represented locations of or environmental conditions around the participant, or any other entertainment element or component. The scent score may include instructions for controllably actuating or modulating the bulk airflow source (FIG. 1B) and the exhaust system (FIG. 1B) at selected times during the scent score timeline.

In embodiments, the scent score timeline is coordinated with a timeline of at least one other delivered component of the scripted entertainment event (e.g., film, amusement park ride, virtual reality simulator, etc.), and the intensity and composition are defined by the scent score to create a representation of scents that would be generated by physical objects represented by the other sequentially delivered component. In such a way, the scent score provides an olfactory story line that can be coordinated with other components (e.g., visual, audio, or haptic stimuli) of the scripted entertainment event to immerse the participant in the entertainment event.

The act 220 of executing the sequence of scent dispersion instructions using one or more scent dispersion devices to produce multiple scents having intensity and composition that vary over time according to the scent score may include executing the scent score with a controller. The controller can direct the scent dispersion system to disperse a plurality of scents into the bulk airflow in the participant environment. The controller may direct the scent distributors to release one or more scents into the bulk airflow according to the scent score timeline, such as by actuating solenoid valves or air sources operably coupled to the respective scent distributors at selected times during the timeline. For example, the controller may send signals to the plurality of scent distributors responsive to executing a computer program having instructions for the same.

In examples, executing the sequence of scent dispersion instructions using one or more scent dispersion devices to produce multiple scents having intensity and composition that vary over time according to the scent score includes executing the sequence of scent dispersion instructions in congruity (e.g., in concert) with a sequence of story elements of a corresponding story script of the entertainment event. For example, the scent dispersion instructions may direct the scent distributors to emit a mixture of two scents having greater amount of a first scent when a first element of the story script is represented as close to the participant (e.g., rider or spectator) and a greater amount of a second scent when a second story element is represented as closer to the participant than the first story element. In examples, executing the sequence of scent dispersion instructions using one or more scent dispersion devices to produce multiple scents having intensity and composition that vary over time according to the scent score includes initiating the sequence of scent dispersion instructions in congruity (e.g., in concert with) with initiation of the entertainment event (e.g., beginning of a film, start of an amusement park ride, etc.).

The act 230 of distributing multiple scents produced by the one or more scent dispersion devices to a participant in the entertainment event includes distributing at least one of the multiple scents in time with a corresponding story element of a corresponding story script for the scripted entertainment event. Each scent dispersion instruction may be congruent in time with a representation of corresponding story element in the story script, such as a representation of one or more of a location, movement between locations, character, physical objects, perceived or apparent distance between the participant and represented physical objects, perceived size of represented physical objects, perceived density of represented physical objects, perceived atmospheric conditions between the participant and the represented physical objects, or perceived obstructions between the participant and the represented physical objects. The perceived characteristics may include the representations of the characteristics in the entertainment environment rather than an actual perception by a participant of the characteristics.

Distributing multiple scents produced by the one or more scent dispersion devices to a participant in the entertainment event includes distributing at least one of the multiple scents with a scent distribution system (FIGS. 1A and 1B) as disclosed, such as via one or more scent distributors. The scent distributors may be actuated according to the scent dispersion instructions of the scent score. In examples, at least some of the scent dispersion instructions correspond to multiple scents and distributing multiple scents produced by the one or more scent dispersion devices includes distributing multiple scents simultaneously such as in a mixture of scents. In examples, distributing multiple scents produced by the one or more scent dispersion devices includes altering a proportion of first scent to second scent over time, such as in congruity with changes in the story script represented in the entertainment (e.g., movement of the participant, change of represented location, introduction of objects, perceived proximity to objects, etc.).

In examples, distributing the multiple scents includes distributing the multiple scents into a passenger area of an amusement park ride. In examples, distributing the multiple scents includes distributing the multiple scents to a seating area of a theatre while displaying a film.

In examples, the method 200 includes selectively removing scents from the entertainment environment, such as by selectively controlling the exhaust system or adding a neutralizing agent to the bulk airflow as disclosed.

Figure 3:
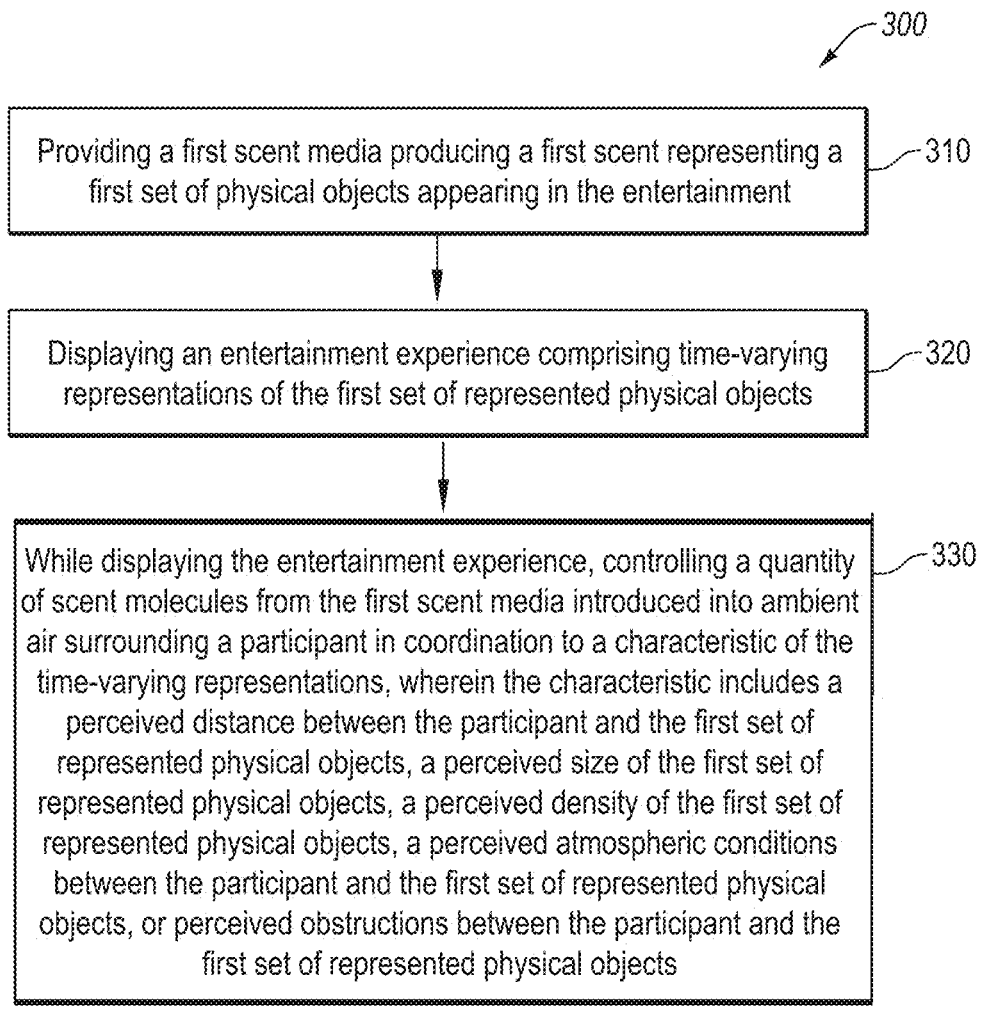
FIG. 3 is a flow diagram of a method of dispersing scents in congruity with entertainment.

FIG. 3 is a flow diagram of a method 300 of dispersing scents in congruity with entertainment. The method 300 includes the act 310 of providing a first scent media producing a first scent representing a first set of physical objects appearing in the entertainment; the act 320 of displaying an entertainment experience comprising time-varying representations of the first set of represented physical objects; and the act 330 of, while displaying the entertainment experience, controlling a quantity of scent molecules from the first scent media introduced into air surrounding a participant in coordination to a characteristic of the time-varying representations, wherein the characteristic includes a perceived distance between the participant and the first set of represented physical objects, a perceived size of the first set of represented physical objects, a perceived density of the first set of represented physical objects, a perceived atmospheric conditions between the participant and the first set of represented physical objects, or perceived obstructions between the participant and the first set of represented physical objects. In embodiments, additional acts may be performed in addition to or in place of the acts 310-330.

The act 310 of providing a first scent media producing a first scent representing a first set of physical objects appearing in the entertainment includes providing a first scent in a first scent distributor where the first scent is associated with the first set of physical objects. The first scent distributor can be part of a scent dispersion system such as the scent dispersion system 100 (FIG. 1A). The first set of physical objects may include physical objects represented in the entertainment event, such as a discrete objects synonymous with a first location, character, condition or other entertainment element. For example, the first location can be a cave, the first set of represented physical objects includes rocks and mud, and the first scent can be a musty or earthy scent. As another example, the first location is a forest or jungle with plants such as trees, and the first scent is a forest or jungle scent (e.g., a scent that smells of one or more plants). In an example, the first location is a mountain or windswept plain with storm clouds and the first scent is a rain scent. In embodiments, providing a first scent media producing a first scent representing a first set of represented physical objects includes providing the first scent media in any of the systems disclosed herein, such as in the first scent source in the first scent distributor. The first scent media provides the source for atomized scent molecules to be mixed with the bulk airflow and additional scents.

In embodiments, the act 320 of displaying an entertainment experience comprising time-varying representations of the first set of represented physical objects includes showing a film, play, or other visual presentation with transitions (e.g., movement, represented proximity, or represented focus) from one location or object to another location or object. For example, displaying an entertainment experience comprising time-varying representations of the first set of represented physical objects includes displaying a film, operating an amusement park ride, performing a play, etc. For example, displaying an entertainment experience comprising time-varying representations of the first set of represented physical objects includes displaying a film or live action depiction featuring a depiction of at least the first set of physical objects (e.g., at a first location) and movement, or shift of represented focus, from the first set of physical objects to at least a second set of physical objects (e.g., at a second location). In embodiments, the act 320 of displaying an entertainment experience comprising time-varying representations of the first set of represented physical objects includes displaying an entertainment experience comprising representations of at least one transition between the first location or objects thereat and the second location or objects thereat. Such examples include moving the participant position from one location to another location, such as by moving a car of an amusement park ride. The entertainment experience is displayed using one or more of a display screen, a projector, a monitor, actors, a stage, a seat, animatronics, an amusement park ride (seat and/or ride enclosure), a theater, etc. In embodiments, the act 320 of displaying an entertainment experience comprising time-varying representations of the first set of represented physical objects includes presenting a representation of an object at different points during the objects' existence, such before fruit is ripe, after the fruit is ripe, and after the fruit is rotten. Each of the time-varying representations of the same object may be associated with a respective and unique scent.

In embodiments, the act 330 of, while displaying the entertainment experience, controlling a quantity of scent molecules from the first scent media introduced into air surrounding a participant in coordination to a characteristic of the time-varying representation, wherein the characteristic includes a perceived distance between the participant and the first set of represented physical objects, a perceived size of the first set of represented physical objects, a perceived density of the first set of represented physical objects, a perceived atmospheric conditions between the participant and the first set of represented physical objects, or perceived obstructions between the participant and the first set of represented physical objects includes controlling the quantity (e.g., relative concentration) of scent molecules from the first scent media with the controller.

In examples, controlling a quantity of scent molecules from the first scent media includes providing an amount of the first scent molecules from the first scent media sufficient to create a perceivable scent evocatively associated with one or more of a story element, a plot line, a character, a location, a memory, an emotion, weather, time, or materials associated with the entertainment experience. For example, controlling a quantity of scent molecules from the first scent media introduced into air includes emitting or otherwise dispersing the first scent molecules into the entertainment environment around the participant congruent with displaying one or more elements of the entertainment experience, such as a representation of an introduction into a location or proximity to objects, characters, etc. In examples, providing an amount of the first scent molecules from the first scent media sufficient to create a perceivable scent evocatively associated with one or more of a story element, a plot line, a character, a location, a memory, an emotion, weather, time, or materials associated with the entertainment experience includes providing an amount of the first scent molecules that is detectable by a human nose, such as subconsciously or consciously perceivable. Controlling a quantity of scent molecules from the first scent media introduced into air includes emitting or otherwise dispersing the first scent molecules into the entertainment environment, such as into the air volume in the entertainment environment, into the air volume introduced into the entertainment environment, into the air volume flowed to or past (e.g., bulk airflow) the participant(s), or into the air volume surrounding the participant.

The method 300 can include providing a second scent media producing a second scent representing a second set of physical objects appearing in the entertainment includes providing a second scent in a second scent distributor where the second scent is associated with the second set of physical objects. The second set of physical objects may include physical objects represented in the entertainment event, such as a discrete objects synonymous with a second location, character, condition or other entertainment element. Providing a second scent media producing a second scent may include distributing a second scent contained in a second scent distributor where the second scent is associated with a set of one or more objects or elements associated with the second location. The second set of represented physical objects can differ from the first set of represented physical objects. For example, the first location may be a cave having rocks and dirt therein, the first scent may be a musty or earthy scent, the second location may be a forest having trees and plants therein, and the second scent may be a tree scent (e.g., pine scent). In embodiments, providing a second scent media producing a second scent includes providing the second scent media in any of systems disclosed herein. The second scent media provides the source for atomized scent molecules to be mixed in the bulk airflow and presented to the participant.

In embodiments, providing a second scent media producing a second scent includes providing at least a second scent media associated with at least a second location or physical objects in the second location, such as a plurality of additional scent media each associated with one of a plurality of additional represented sets of physical objects (or entertainment elements such as characters, objects in a scene, etc.). For example, any number of scent media can be provided, such as 2, 3, 4, 5, 6, 8, 10 or more distinct scent media, to produce a corresponding number of distinct scents or combinations thereof. In embodiments, providing at least a second scent media includes providing more than one scent media, where the mixture of the scents in the more than one scent media are associated with at least a second location or physical objects in the second location.

In examples, the method 300 further includes, while displaying the entertainment experience, controlling a quantity of scent molecules from the second scent media introduced into air surrounding a participant in coordination to a characteristic of the time-varying representation, wherein the characteristic includes a perceived distance between the participant and the second set of represented physical objects, a perceived size of the second set of represented physical objects, a perceived density of the second set of represented physical objects, a perceived atmospheric conditions between the participant and the second set of represented physical objects, or perceived obstructions between the participant and the second set of represented physical objects.

In examples, the method 300 includes, while displaying the entertainment experience, controlling a quantity of scent molecules from the first scent media and a quantity of second scent molecules from the second scent media introduced into air surrounding a participant in coordination to a characteristic of the time-varying representation. Controlling a quantity of scent molecules from the first scent media and controlling a quantity of scent molecules from the second scent media may include providing an amount of the first scent molecules from the first scent media and the second scent molecules from the second scent media in relative proportions (e.g., concentrations) sufficient to create a perceivable scent evocatively associated with one or more of a story element, a plot line, a character, a location, a memory, an emotion, weather, time, or materials associated with the entertainment experience.

In examples, while displaying the entertainment experience, controlling a quantity of scent molecules from the first scent media or the second scent media introduced into air (e.g., bulk airflow) surrounding a participant includes using any of the scent blending systems disclosed herein. Controlling a quantity of scent molecules from the first scent media or the second scent media introduced into air includes operating the plurality of scent dispersion devices to emit a selected amount (e.g., concentration) of scent molecules, respectively. For example, the quantity the scent molecules, and duration of time the scent molecules, are emitted from the first scent media and the second scent media can be selectively and automatically controlled by the controller, such as according to a timeline. The timeline may be congruous with or synchronized with the time-varying entertainment. For example, the scents are emitted congruously with the display of selected objects or elements of the entertainment experience.

Various aspects of controlling a quantity of scent molecules from the first scent media or the second scent media are described herein. It is understood that any aspect disclosed with respect to a single scent media and set of scent molecules can also respectively apply to every other scent media and set of scent molecules unless context dictates otherwise.

In embodiments, controlling a quantity of scent molecules from the first scent media and the second scent media includes mixing a plurality of first scent molecules from the first scent media and a plurality of second scent molecules from the second scent media in proportion to a perceived or apparent distance between the first and second sets of represented physical objects, such as while a focus of the entertainment experience transitions between a first and a second represented set of objects or locations. For example, controlling a quantity of scent molecules from the first scent media and the second scent media includes providing an amount of one or more of a plurality of first scent molecules from the first scent media and a plurality of second scent molecules from the second scent media in proportion to (and congruous with) a focus of the entertainment experience on one or more sets of physical objects present in the first location or the second location represented in the entertainment. For example, a skunk may be present in the first location but absent or in the second location and the first scent may include a skunk scent, and controlling the quantity of scent molecules from the first and the second scent media may include providing a greater amount of the skunk scent when the skunk is the focus of the entertainment than when the skunk is not the focus or absent from the entertainment. In embodiments, the magnitude (e.g., amount) of scent is proportional to the participant's represented distance from a perceived source and more scent (e.g., greater amount) is emitted when the depiction is close to the perceived source (e.g., object(s), location, etc.).

Controlling the quantity of scent molecules from the first and the second scent media may include mixing a plurality of first scent molecules from the first scent media and a plurality of second scent molecules from the second scent media in proportion to a distance between the first and second locations while a focus of the entertainment experience transitions between the first and second location. The mixing can include providing a plurality of pulses of one or more of the first scent and the second scent. For example, at a first point (e.g., nearer the first represented set of objects or location in the entertainment) a greater amount and/or duration of pulses of the first scent is mixed with a lesser amount and/or duration of pulses of the second scent, during a transition between the first point and the second point (e.g., nearer the represented second set of objects or location in the entertainment) the amount and/or duration of pulses of the first scent is decreased as the amount and/or duration of pulses of the second scent is increased, and at a second point a lesser amount and/or duration of pulses of the first scent is mixed with a greater amount and/or duration of pulses of the second scent. Accordingly, the scent(s) are transitioned in congruity with transition between visual, audio, and/or haptic (e.g., tactile) components of entertainment.

A larger amount of scent may be provided upon introducing a location or entertainment element to help ensure an association of the scent with the location. For example, a greater proportion of a selected scent may be delivered to the entertainment environment upon introduction to a location or a story element entering the location associated with the selected scent, after which the amount of the scent may be tapered to a lower amount upon dwelling in the location or transitioning to a second location.

The scent(s) may be provided in one or more pulses. In examples, controlling a quantity of scent molecules from the first scent media and controlling a quantity of scent molecules from the second scent media includes providing an amount of one or more of a plurality of first scent molecules from the first scent media or a plurality of second scent molecules from the second scent media by providing one or more of at least one pulse of the first scent molecules or at least one pulse of the second scent molecules to the bulk airflow or (ambient) air volume surrounding the participant. The pulses can vary in duration and/or pressure (e.g., air volume). In embodiments, the pulses can be provided in a duration of at least about 0.01 seconds (s) or more, such as about 0.05 s, about 0.07 s, about 0.1 s, about 0.2 s, about 0.3 s, about 0.4 s, about 0.5 s, about 0.7 s, about 0.8 s, about 1 s, about 1.5 s, about 1.8 s, about 2 s, about 2.2 s, about 5 s, or ranges between any combination of the foregoing. Shorter pulses, even from a single scent media, may provide a different scent profile than longer pulses. Longer scent pulses may provide a more intense scent profile. The pulses can be provided at a pressure of about 1 psi or more, such as about 5 psi, about 10 psi, about 12 psi, about 15 psi, about 18 psi, about 20 psi, about 25 psi, about 30 psi, about 50 psi, about 70 psi, about 100 psi, or ranges between any combination of the foregoing. Any combination of pulse duration and pressure can be used to provide scent from the scent distributors. In embodiments, the pulse duration and pulse pressure used to provide the first scent and the second scent (e.g., additional scents) are identical. In embodiments, one or more of the pulse duration or pulse pressure used to deliver first scent from the scent distributor differs from one more of the pulse duration or pulse pressure used to deliver the second scent (e.g., additional scents) from the second (e.g., additional) scent distributor.

The pulses are controlled by the controller and may be delivered by any of the scent distributors or systems disclosed herein. In embodiments, controlling a quantity of scent molecules from the first scent media and controlling a quantity of scent molecules from the second scent media includes providing an amount of one or more of a plurality of first scent molecules from the first scent media or a plurality of second scent molecules from the second scent media by providing one or more of at least one pulse of the first scent molecules or at least one pulse of the second scent molecules to the air volume surrounding the participant or bulk airflow. For example, controlling a quantity of the scent molecules from the first scent media or second scent media includes releasing (e.g., forcing) one or more of a selected amount (e.g., volume or weight) of scent molecules from the first scent media and a selected amount of scent molecules from the second scent media during a selected duration, such as in one or more pulses. For example, during a 1 s time frame, a 1 s pulse of the first scent may be released and a 0.1 s pulse of the second scent may be released. Accordingly, a mixture of the first and second scents may be predominantly (or even entirely) the first scent. During a transition, the pulse time of the first scent may be decreased and the duration of pulses of the second scent may be increased until the mixture of scents is predominantly or entirely the second scent. In examples, the number of pulses is used to control the release or mixture of one or more of the first scent and the second scent. For example, during a focus on the represented first set of objects or at a first location in the entertainment the first scent may be released at a rate of 5 pulses per second while the second scent may be released at a rate of 0 or 1 pulses per second. Upon transition, in the entertainment, from the focus on the represented first set of objects or the first location to the represented second set of objects or the second location, the first scent may be released at a decreasing rate of pulses per second while the second scent may be released at an increasing rate of pulses per second until the mixture of scents is predominantly or entirely the second scent.

More than two scents can be mixed as disclosed above. In some embodiments, controlling a quantity of scent molecules from the first scent media and the at least a second scent media introduced into air volume (e.g., bulk airflow) surrounding the participant includes blending two or more scents to form a new scent from the combination of two or more scents. For example, a water scent and a musty or earth scent may be mixed to form a cave scent. The amount of the scent(s) used to combine into a new combination scent may be selectively controlled by the controller (FIG. 1A) and may also be transitioned (e.g., increased or decreased) from one represented set of objects or locations to another in the entertainment experience.

In embodiments, controlling a quantity of scent molecules from the first scent media and the second scent media includes providing an amount of one or more of a plurality of first scent molecules from the first scent media or a plurality of second scent molecules from the second scent media in proportion(s) to evoke a scent associated with one or more of a story element, a plot line, a character location, a memory, an emotion, weather, time, or materials associated with the entertainment experience. For example, controlling a quantity of scent molecules from the first scent media and the second scent media may include providing an amount of one or more of a plurality of first scent molecules from the first scent media or a plurality of second scent molecules from the second scent media in proportion(s) to emit a scent or combination of scents to evoke a memory, emotion, or subconscious response to the scent to cause a participant to recall or associate the corresponding point in the entertainment with the story element, plot line, character location, memory, emotion, weather, time, or materials. For example, one or more scents can be emitted into the participant environment in amounts above a threshold of human detection but below an amount that is consciously perceivable. For example, scents can be detected but may not be noticed to by the conscious mind of the average human in a given moment if the mind is distracted by a more stimulating component of entertainment such as a loud blast or a visual car crash. Additionally, some scents at any level may not be identified clearly by the brain of an average human until a visual or audible piece of information is added to the experience, making the scent considered undetectable. The scent(s) may be distributed at such small levels to be below, on, or over the line of consciously detectable concentrations to enhance the visual and haptic (e.g., sense of place or immersion). Such limited concentrations can be distributed to the participant to provide an additional sensory input for the participant but not distract the participant from the visual, audio, or haptic components of the entertainment experience.

The threshold for conscious detection of a scent or scents (e.g., odor recognition threshold) may be 0.001 ppm or more, such as 0.001 ppm to 0.1 ppm, 0.1 ppm to 1 ppm, 1 ppm to 10 ppm, 10 ppm to 50 ppm, 50 ppm to 100 ppm, 100 ppm or more, 50 ppm or more, 10 ppm or more, 1 ppm or more, less than 100 ppm, less than 50 ppm. Any of the scents can be delivered below, at, or above any of the threshold amounts disclosed herein according to the desired impact on the participant and additional sensory inputs of the entertainment. Scents at concentrations below the threshold level (e.g., below the odor recognition threshold) may be detected by the limbic system and trigger a response in the brain of a participant such as an association, emotion, or memory, but may not be consciously detected or perceived by a participant. Such levels of scents are above the odor detection threshold (e.g., concentration at which an average human can detect the scent) but below the odor recognition threshold (e.g., consciously perceivable or detectable concentration where a scent is recognized). The odor recognition threshold may be at least 2 to 5 times higher than the odor detection threshold. Accordingly, scents can be selectively delivered at levels 2 to 5 times lower than the thresholds for conscious detection to cause the limbic system to respond without causing a perceivable recognition of the scent in the mind of a participant. It should be understood that the threshold of conscious detection of a scent can be effected by numerous factors such as the species and properties of scent molecules, sensory input from other senses, volume of air in an environment, movement of air in an environment (e.g., wind), other scents in the environment, etc. In embodiments, controlling a quantity of scent molecules from the first scent media and the second scent media includes providing an amount of one or more of a plurality of first scent molecules from the first scent media or a plurality of second scent molecules from the second scent media above an amount that is consciously perceivable by a participant (e.g., above the odor recognition threshold), such as above a baseline or threshold amount. Accordingly, the scent(s) can be blended or transitioned to non-visually transition the participant from one element to another element in the entertainment.

In embodiments, the method 300 may include providing one or more additional (e.g., a third, fourth, fifth, etc.,) scent media in scent distributors associated with one or more additional (e.g., third, fourth, fifth) represented sets of objects, locations, or elements in the entertainment. In such embodiments, the method 300 further includes, while displaying the entertainment experience, controlling a quantity of scent molecules from the one or more additional scent media introduced into bulk airflow or air volume surrounding a participant in coordination to a characteristic of the time-varying representation includes using any of the scent blending systems disclosed herein. The characteristic includes a perceived distance between the participant and the additional set of represented physical objects, a perceived size of the additional set of represented physical objects, a perceived density (e.g., number of objects in a space) of the additional set of represented physical objects, a perceived atmospheric conditions between the participant and the additional set of represented physical objects, or perceived obstructions between the participant and the additional set of represented physical objects.

In embodiments, displaying entertainment experience comprising representations of at least one transition between the first location and the second location and controlling a quantity of scent molecules from the first scent media and the second scent media are conducted according to a common time scheme (e.g., same timeline). For example, the controller (FIG. 1A) can coordinate the movements, transitions, displays, or the focus of the entertainment experience with the delivery/mixing of one or more scents to the participant to occur congruently (e.g., contemporaneously or synchronously). The scent distribution system can be operated on the timeline such that the emission of the scents are congruous with associated entertainment elements which are also displayed on the same timeline.

In embodiments, the delivery of a plurality of scents heightens the participant's experience during a display of an entertainment experience, such as by providing a more primal and even subconscious means of associating story elements in mind of the participant.

The method 300 allows artistic introduction, blending, and presentation of scents in congruity with objects in the entertainment experience. For example, a visual scene may include 5 objects and each object is associated with a unique scent from among a scent palette. The method 300 provides for visual and olfactory representation of the 5 objects as a whole by presentation of the entire scent palette (e.g., a mixture of all 5 scents) with the scene. The method 300 also allows visual and olfactory highlighting of each of the 5 objects in a unique way to further immerse the participant in the visual scene. For example, as the focus of the entertainment shifts to one object, the scent associated with the object may be increased and the scents of the other objects may be decreased or eliminated. Further, as the focus shifts to another object, the plurality of scents can be emitted in various mixtures (e.g., relative proportions) to provide olfactory transitions from one object to another, such as by reducing the first scent while increasing a second scent congruently with the change of focus from the first object (or location) to the second object (or location). In such a way, the method 300 allows for immersive entertainment experiences with films, static images, plays, amusement park rides, etc. For example, a display of a bowl of fruit (e.g., sculpture or static image) can be transformed into an immersive experience by selectively highlighting the each species of fruit with associated scent(s), such as while providing narration about or focus on the species.

Further, when used congruently with visual, audio, or haptic presentations a single scent can be used to represent a plurality of different objects. For example, while a cave is depicted an earth scent is emitted, and while an animal is depicted the earth scent is emitted again, but a participant may perceive the same earth scent differently in view of the different visual, audio, or haptic sensory inputs congruently provided.

The method 300, can be implemented in virtual reality or augmented reality experiences. A virtual reality headset may be coupled to a controller which coordinates the delivery of scents into a virtual reality presentation environment responsive to the objects encountered or depicted in the virtual reality experience. For example, a first scent is introduced while the virtual reality participant is viewing a first object and the first scent blends to a second scent when the virtual reality participant moves within the virtual reality experience to a view a second object. Accordingly, the scents can be controllably delivered to the participant (e.g., have the magnitude controlled or number of scents blended) based on the participant's unique experience in the virtual reality entertainment. The scents can be provided to the virtual reality presentation environment as a whole, or may even be directed through the headset directly to the participant (e.g., where the headset carries or is coupled to scent distributors).

Figure 4:
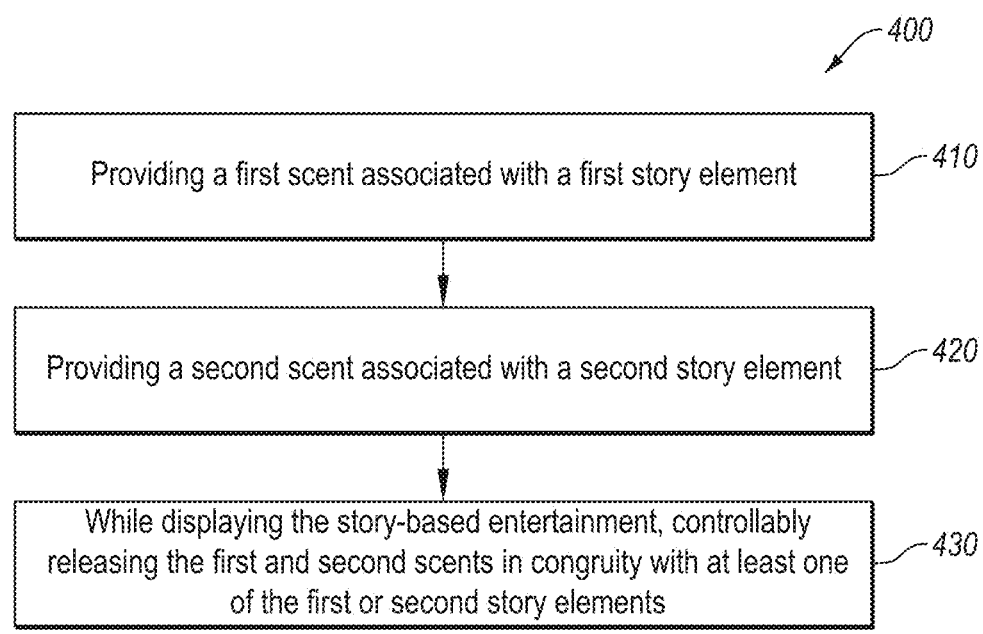
FIG. 4 is a flow diagram of a method of dispersing scents in congruity with story-based entertainment.

FIG. 4 is a flow diagram of a method 400 of dispersing scents in congruity with story-based entertainment, according to an embodiment. The method 400 includes an act 410 of providing a first scent associated with a first story element; the act 420 of providing a second scent associated with a second story element; and the act 430 of, while displaying the story-based entertainment, controllably releasing the first and second scents in congruity with at least one of the first or second story elements.

In embodiments, 410 providing a first scent associated with a first story element includes providing the first scent that corresponds to (e.g., is commonly associated with) a story element. In examples, story elements include any portions of the entertainment experience such as characters, locations, animals, plants, foods, items, or any other element displayed to the participant in the entertainment experience. For example, the first scent may be a rose scent and the first story element may be a rose bush or garden. In examples, the first scent may be provided in any of the systems disclosed herein, such as in a scent media of a scent source of a scent distributor.

In embodiments, 420 providing a second scent associated with a second story element includes providing the second scent that corresponds to a story element that is different than the first story element. For example, 420 providing a second scent associated with a second story element may include providing the second scent where the second scent is different from the first scent and the second story element is different than the first story element. For example, the second story element may be a pine tree and the second scent may be a pine tree scent. The second scent may be provided in any of the systems disclosed herein, such as in a scent media of a scent source of a scent distributor.

In embodiments, 430 while displaying the story-based entertainment, controllably releasing the first and second scents in congruity with at least one of the first or second story elements includes releasing one or both of the first and second elements in selected amounts (e.g. volumes), such as by pulsing the first and/or second scent(s) for selected durations. The amounts and/or durations may be similar or identical to those disclosed above with respect to the method 300. The amounts and/or durations can direct a participant's attention to the first or second story elements. For example, while displaying the story-based entertainment, controllably releasing the first and second scents in congruity with at least one of the first or second story elements may include providing the first scent while the first story element is displayed, providing the second scent while the second story element is displayed, and providing a mixture of both scents while transitioning from the display of the first story element to the second story element.

In embodiments, controllably releasing the first and second scents in congruity with at least one of the first or second story elements includes controllably releasing an amount of one or more of the first or second scents that is inversely related (e.g., proportional) to an intended amount of evoked response (e.g., emotion) of the correspondingly displayed story-based entertainment at a time of release of the first or second scents. For example, an amount of the first scent may be reduced at a time of heightened emotional content in the entertainment and raised at with the display of non-emotional content. The emotional content may include a depiction of one or more story elements designed to induce one or more of excitement, laughter, happiness, sadness, etc., in the participant. Such configurations can provide increased olfactory stimulation during less emotional portions of the entertainment and less olfactory stimulation during more emotional portions of the entertainment, such as when the sense of smell may be overshadowed by other senses.

In embodiments, controllably releasing the first and second scents in congruity with at least one of the first or second story elements includes controllably releasing an amount of one or more of the first or second scents that is above an amount that is detectable by an average human but below an amount that is consciously perceivable by the average human (e.g., participant), such as below the odor recognition threshold as disclosed above. For example, the brain may detect an amount of scent in the environment of a participant which may trigger a memory response without the participant realizing that the scent is in the air or recognizing the scent (e.g., without consciously perceiving the scent). In embodiments, controllably releasing the first and second scents in congruity with at least one of the first or second story elements includes controllably releasing an amount of one or more of the first or second scents that is above an amount that is consciously perceivable by a participant, such as above the threshold amount. For example, it may be desirable to provide a scent or mixture of scents to the participant environment in an amount that can trigger a conscious recognition of the scent(s) in the mind of a participant, such as to consciously associate an element with a scent or transition from one element to another element (e.g., location). Such association can direct the attention of a participant to selected entertainment elements based on scent.

In embodiments, the scents are controllably released (e.g., mixed) to teach a participant to associate the scents with one or more elements of the entertainment experience. For example, while displaying the story-based entertainment, controllably releasing the first and second scents in congruity with at least one of the first or second story elements may include providing the first scent while displaying the first story element and providing the second scent while displaying the second story element to train a participant to associate the first and second scents with the first and second story elements. The training can be carried out during an initial part of the story-based entertainment.

The method 400 may include providing one or more additional (e.g., a third, fourth, fifth, etc.) scents, such as in scent distributors associated with one or more additional (e.g., third, fourth, fifth) locations or elements in the story-based entertainment. In such embodiments, the method 400 further includes, while displaying the story-based entertainment, controllably releasing the one or more additional scents in congruity with one or more additional story elements. Any number of scents can be blended or transitioned to correspond to one or more story elements or transitions. In embodiments, the method 400 may include using any of the scent blending systems disclosed herein.

In embodiments, displaying the story-based entertainment and controllably releasing the first and second scents in congruity with at least one of the first or second story elements are congruous with a common time scheme. For example, the controller (FIG. 1A) may coordinate the movements (of the participant position), transitions, displays, or the focus of the entertainment experience with the delivery/mixing of one or more scents to the participant to occur congruently or synchronously.

Figure 5:
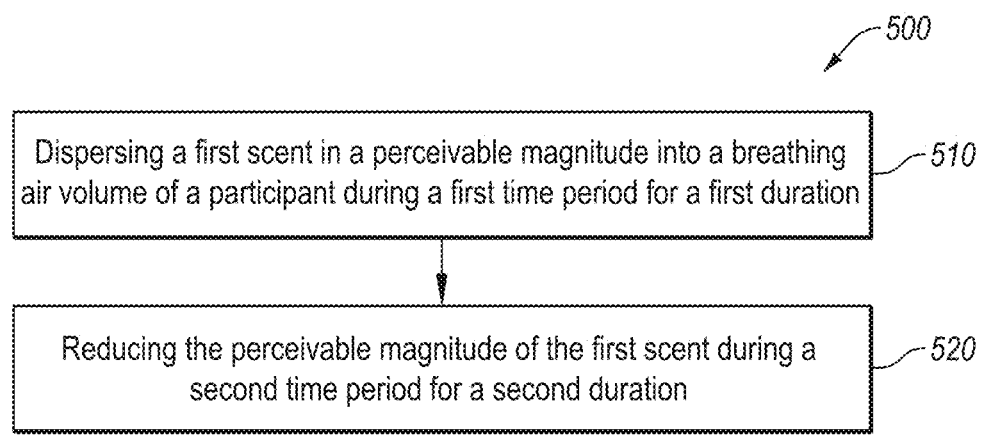
FIG. 5 is a flow diagram of a method of creating a time-varying scent experience.

A scent may be neutralized or reduced in magnitude in the entertainment environment. FIG. 5 is a flow diagram of a method 500 of creating a time-varying scent experience, according to an embodiment. The method 500 includes the act 510 of dispersing a first scent in a perceivable magnitude into a breathing air volume of a participant during a first time period for a first duration, and the act 520 of reducing the perceivable magnitude of the first scent during a second time period for a second duration.

The act 510 of dispersing a first scent in a perceivable magnitude into a breathing air volume of a participant during a first time period for a first duration may be similar or identical to the acts 340 or 430 disclosed herein. For example, dispersing a first scent in a perceivable magnitude into a breathing air volume of a participant during a first time period for a first duration may include releasing or forcing atomized first scent molecules from a first scent distributor into the bulk airflow around the participant, such as with any of the systems disclosed herein. The perceivable magnitude of a scent or scents can be at or above any of the odor detection thresholds or odor recognition thresholds disclosed herein. For example, dispersing a first scent in a perceivable magnitude into a breathing air volume of a participant during a first time period for a first duration may include dispersing the first scent into the air volume above a threshold amount consciously perceivable by an average human. In embodiments, dispersing a first scent in a perceivable magnitude into a breathing air volume of a participant during a first time period for a first duration includes dispersing the first scent into the air volume above a threshold amount that can produce a subconscious reaction of the first scent in the mind of a participant (e.g., above the odor detection threshold) but below a threshold amount that is consciously perceivable by the participant (e.g., below the odor recognition threshold).

The act 520 of reducing the perceivable magnitude of the first scent during a second time period for a second duration includes reducing or eliminating the concentration of the first scent in the breathing air volume by one or more of removal or chemical reaction. The act 520 controllably decreases the concentration of scent molecules perceived by the participant. One way of decreasing the concentration is to remove a volume of air in which the scent molecules are dispersed away from the participant. For example, reducing the perceivable magnitude of the first scent during a second time period for a second duration may include evacuating the breathing air volume carrying the first scent from the entertainment environment. Evacuating the first scent from the breathing air volume (e.g., bulk airflow or environment of the participant) may include using the exhaust system 145 (FIG. 1A) to remove the breathing air volume from the entertainment environment, such as prior to replacing the breathing air volume with a second breathing air volume containing no scent or new scent(s). For example, evacuating the first scent from the breathing air volume can include operating the exhaust system for a selected duration prior to adding any new scent(s) to the breathing air volume (e.g., entertainment environment) surrounding a participant.

In examples, the act 520 of reducing the perceived magnitude includes introducing a neutralizing agent into the breathable air volume. Introducing the neutralizing agent into the air volume will render scent molecules imperceptible, such as by chemically reacting, binding, or sequestering the scent molecules with the neutralizing agent. Introducing the neutralizing agent into the breathable air volume may include dispersing the neutralizing agent from any of the systems disclosed herein, such as via a respective scent distributor containing the neutralizing agent. The neutralizing agent may be released from the scent distributor in a similar or identical manner as the scents. For example, prior to or during a transition from one element to another element in an entertainment experience, the neutralizing agent may be pulsed into the bulk airflow. The neutralizing agent may be specifically composed to neutralize one or more scents or combinations thereof, such as terpene-containing or cyclodextrine-containing materials, etc. In embodiments, dispersing a neutralizing agent into the air volume while transitioning from the first portion of the entertainment to a second portion the entertainment includes dispersing the neutralizing agent into the bulk airflow in an amount effective to render to the first scent or one or more scents in the entertainment environment consciously unperceivable to a participant (e.g., reduce the amount free scent molecules below a threshold level).

The method 500 may include dispersing at least a second scent in a perceivable magnitude into a breathing air volume of a participant during the first time period or at least a third time period for a third duration. Dispersing at least a second scent in a perceivable magnitude into a breathing air volume of a participant is similar or identical to dispersing the first scent in a perceivable magnitude into a breathing air volume of a participant in one or more aspects. The second scent can be dispersed after the first scent is removed. For example, the method 500 may include dispersing at least one new scent into the air volume during a transition to a new location or element in the entertainment, after reducing the perceivable magnitude of the first scent during the second time period for a second duration. Such embodiments further include reducing the perceivable magnitude of the first scent while transitioning from the second portion of the entertainment to an additional portion the entertainment. Accordingly, a plurality of scents can be dispersed into and reduced or removed in the entertainment environment, such as to quickly (and sequentially) disperse and eliminate scents to keep up with visual transitions in an entertainment experience (e.g., visual transitions represented in a visual medium).

Figure 6:
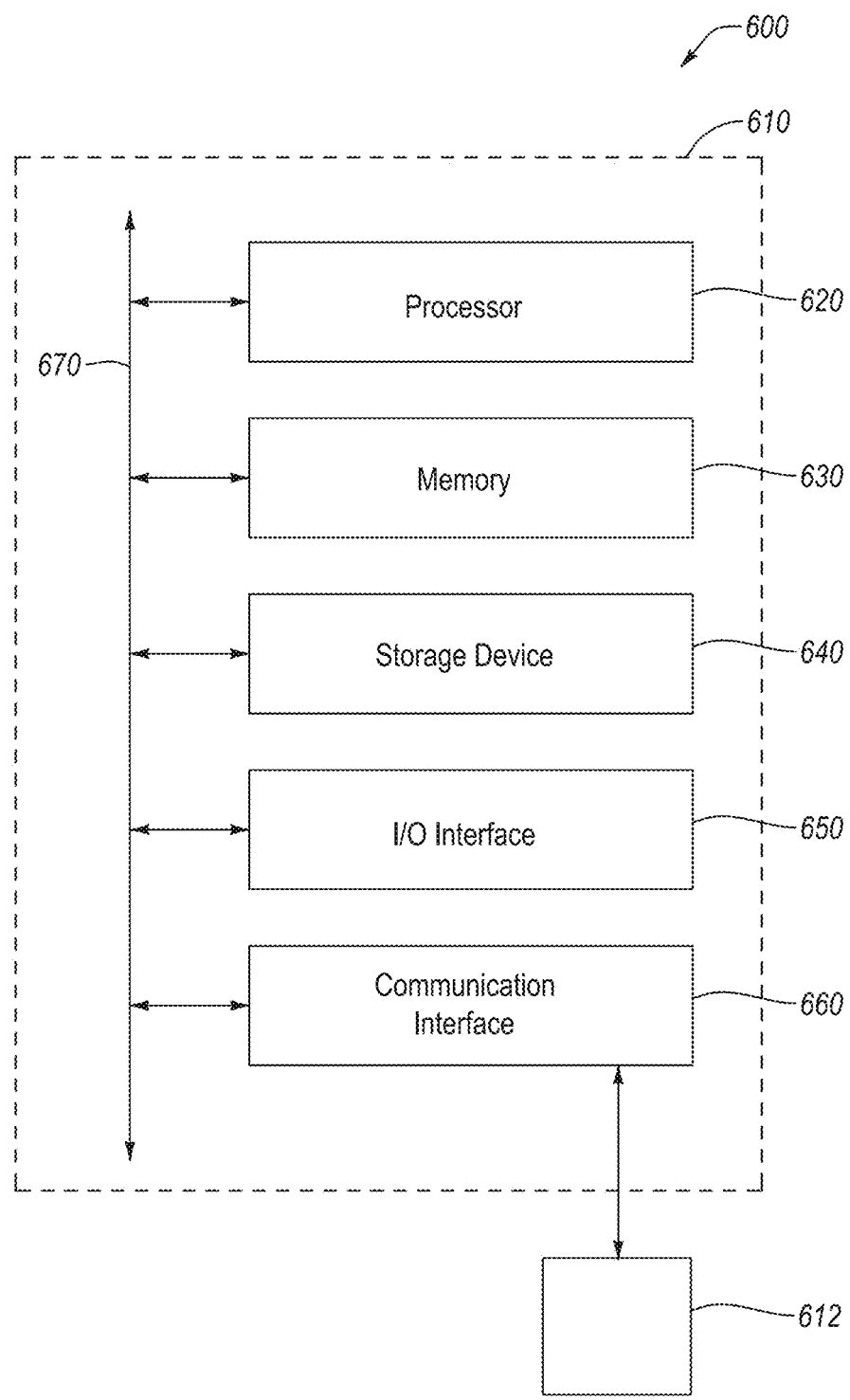
FIG. 6 is a schematic of a controller for executing any of the example methods disclosed herein.

Any portions of any of the methods disclosed herein may be directed or performed by a controller (FIG. 1A) of any of the systems disclosed herein. FIG. 6 is an example of a controller 600 for executing any of the example methods disclosed herein. The controller 600 includes at least one computing device 610. The at least one computing device 610 is an exemplary computing device that may be configured to perform one or more of the acts described above, such as the method 200, 300, 400, or 500. The at least one computing device 610 can include one or more servers, computers (e.g., desk-top computer, lap-top computer), or mobile computing devices (e.g., smartphone, tablet, etc.). The computing device 610 includes at least one processor 620, memory 630, a storage device 640, an input/output ("I/O") device/interface 650, and a communication interface 660. Additional or alternative components may be used in some examples. Further, in some examples, the controller 600 or the computing device 610 can include fewer components than those shown in FIG. 6.

In some examples, the processor(s) 620 includes hardware for executing instructions (e.g., instructions for carrying out one or more portions of any of the methods disclosed herein), such as those making up a computer program. In particular examples, processor(s) 620 may include one or more internal caches containing instructions, such as copies of instructions in memory 630 or storage device 640. In some examples, the processor 620 may be configured to automatically perform any portions of any of the methods disclosed herein, such as to adjust the amount of scent(s) released or initiate an entertainment experience.

The processor(s) 620 are operably coupled to the memory 630. The memory 630 may be used for storing data, metadata, and programs for execution by the processor(s) 620. The memory 630 may include one or more of volatile and non-volatile memories, such as Random Access Memory (RAM), Read Only Memory (ROM), a solid state disk (SSD), Flash, Phase Change Memory (PCM), or other types of data storage. Operational programs (e.g., scent scores) encoding the methods disclosed herein may be stored in the memory 630 or the storage device 640. In some examples, the storage device 640 includes a non-transitory memory storage medium, such as a hard disk drive (HDD), a floppy disk drive, flash memory, an optical disc, a magneto-optical disc, magnetic tape, or a Universal Serial Bus (USB) drive or a combination of two or more of these.

The I/O devices/interfaces 650, allow a user to provide input to, receive output from, and otherwise transfer data to and from the computing device 610. These I/O devices/interfaces 650 may include a mouse, keypad or a keyboard, a screen, audio speakers, a touch screen, camera, optical scanner, network interface, web-based access, modem, a port, other known I/O devices or a combination of such I/O devices/interfaces 650.

The communication interface 660 can include hardware, software, or both. The communication interface 660 can provide one or more interfaces for communication (such as, for example, packet-based communication) between the computing device 610 and one or more additional computing devices 612 or one or more networks. For example, communication interface 660 may include a network interface controller (NIC) or network adapter for communicating with an Ethernet or other wire-based network or a wireless NIC (WNIC) or wireless adapter for communicating with a wireless network, such as a WI-FI. The bus 670 can include hardware, software, or both that couples components of computing device 610 to each other.

In embodiments, the controller 120 (FIG. 1A) may be configured as the controller 600. The controller 600 may include one or more operational programs or computer program products (e.g., scent scores) for carrying out any of the method or portions thereof described herein.

Figure 7:
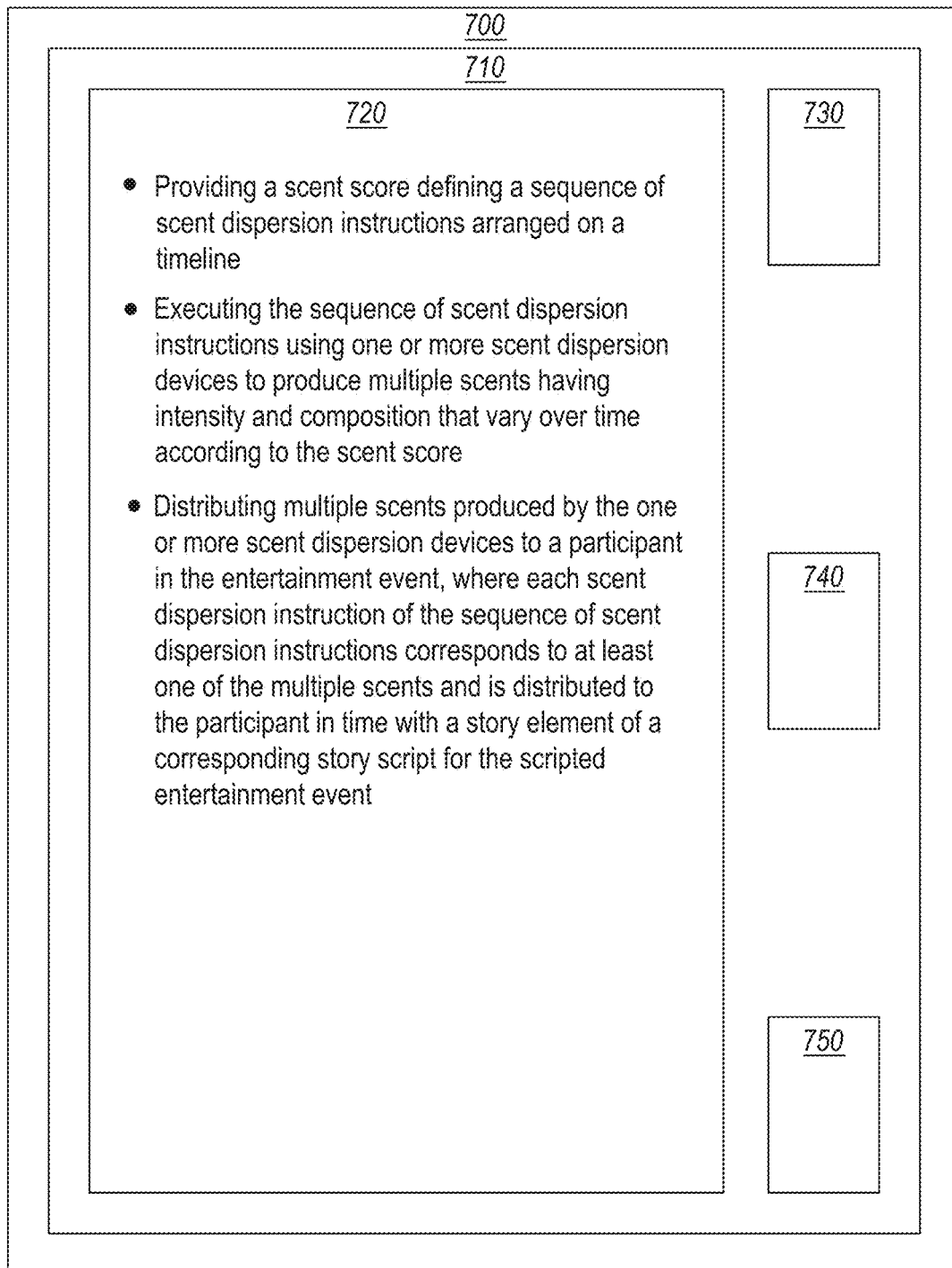
FIG. 7 is a block diagram of an example computer program product.

FIG. 7 is a block diagram of an example computer program product 700. The computer program product 700 is arranged to store instructions for a method of dispersing scent in congruity with entertainment, a method of dispersing scent in congruity with story-based entertainment, or a method of dispersing scent in congruity with entertainment as disclosed with respect to the methods 200, 300, 400, and 500. The non-transitory signal bearing medium 710 may include a computer-readable medium 730 (e.g., read-only memory, RAM, hard drive such as a magnetic disc drive or solid state disc, flash memory stick, internal cache of a processor, or optical disc), a computer recordable medium 740 (e.g., RAM, hard drive, memory stick, optical disc, etc.), a computer communications medium 750 (e.g., internal cache of a BUS, etc.), or combinations thereof, stores programming instructions 720 (e.g., computer code) that may configure the processing unit of an associated computer storing the same to perform all or some of the methods or acts described herein.

The instructions may include, for example, one or more machine readable and executable instructions for "method for providing time-varying scent effects in a scripted entertainment event." These instructions may include, for example, one or more machine readable and executable instructions for "providing a scent score defining a sequence of scent dispersion instructions arranged on a timeline." The instructions may include, for example, one or more machine readable and executable instructions for "executing the sequence of scent dispersion instructions using one or more scent dispersion devices to produce multiple scents having intensity and composition that vary over time according to the scent score." The instructions may include, for example, one or more machine readable and executable instructions for "distributing multiple scents produced by the one or more scent dispersion devices to a participant in the entertainment event, where each scent dispersion instruction of the sequence of scent dispersion instructions corresponds to at least one of the multiple scents and is distributed to the participant in time with a story element of a corresponding story script for the scripted entertainment event." In some embodiments, the instructions may include any portions of the methods disclosed herein, in any combination.

The instructions may include one or more machine readable and executable instructions for dispersing scents in time with an entertainment experience. For example, the instructions may include a scent score for a scripted entertainment event (e.g., entertainment experience). The scent score includes a sequence of scent dispersion instructions arranged on a timeline. The sequence of scent dispersion instructions is executable by one or more scent dispersion devices to distribute one or more scents. Each scent dispersion instruction of the sequence of scent dispersion instructions may correspond to at least one of the one or more scents and may be aligned in time with a story element of a corresponding story script for the scripted entertainment event. For example, each scent dispersion instruction of the scent score may correspond to presence of the entertainment (e.g., participant position) in a location, presence of an item or character in a location, transition from one element (or component) to another element (or component), or any other entertainment premise. In examples, the scent dispersion instructions include instructions to disperse more than one scent congruously (e.g., in concert with each other, simultaneously, etc.), such as to mix scents as disclosed herein. In embodiments, the scent score includes instructions to speed or slow the bulk airflow in the entertainment environment. The scent score may include scent dispersion instructions to transition scents as disclosed herein. Accordingly, the scent score can selectively control the use (e.g., dispersion) of scents from the scent palette, such as on a timeline, congruously with the representation of elements of the scripted entertainment event. The scent score may include scent dispersion instructions adapted to operate any of the systems by any of the methods disclosed herein.

In embodiments, the scripted entertainment event is an amusement park ride. In embodiments, the scripted entertainment event is a film, a play, a tour, or video presentation. In embodiments, the scent dispersion instructions in the scent score are synchronized with a timeline of movements and/or visual displays of the amusement park ride, film, or any other entertainment event or experience.

The above instructions are exemplary, and in embodiments, any of the methods or acts thereof may be included in a computer program product that is executable by any of the controllers of any of the systems disclosed herein.

CONCLUSION

It should be noted that while the present disclosure focuses on controllably emitting scents in congruity with specific elements or components in entertainment, the systems and methods described herein may be used in many other applications or fields. For example, the entertainment environment may be a learning environment or a healthcare environment and the entertainment may be an instructional experience (e.g., film, demonstration, or lecture) or a healthcare experience (e.g., relaxation film or visual treatment). In particular, the systems and methods for selectively emitting a plurality of scents described herein can be used to emit a plurality of scents in congruity with an experience (e.g., tour, educational program, etc.) in a selected manner. As such, the discussion of any particular embodiment is meant as illustrative only.

Additionally, while the system has been discussed with reference to thematic uses, the scent dispersion system may also be used to enhance olfactory characteristics of areas, such as outdoor areas, indoor venues, and the like. For example, systems and methods disclosed herein can include providing a selected level of scent(s) into an outdoor environment (e.g., selected outdoor air volume) to emulate scents from objects in the outdoor environment. Accordingly, an outdoor environment composed of artificial objects or recreations of objects can be made to appear more realistic by presenting scents associated with the location, time, or objects therein. In embodiments, the systems and methods disclosed herein selectively emit creosote scents to emulate a cabin scent, leather scent to emulate a leather goods section of a shop, flow scent(s) to emulate flower bed scent, burning coal scent to emulate a train exhaust or boiler, etc. The scent distributors can be located proximate to the objects or locations which the corresponding scents are intended to represent. The different scents can be individually introduced, blended to transition from one scent to another, or combined to provide an olfactory presentation of more than one object or location, all in an outdoor environment. Accordingly, scents can be provided in outdoor environments to heighten the experience of being in the outdoor location by emulating what a time, location, or objects therein should smell like.

In methodologies directly or indirectly set forth herein, various steps and operations are described in one possible order of operation, but those skilled in the art will recognize the steps and operation may be rearranged, replaced or eliminated without necessarily departing from the spirit and scope of the present invention. Any elements or aspects of specific methods or systems disclosed herein may be used with any of the other methods or systems disclosed herein. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for providing time-varying scent effects in a scripted entertainment event, the method comprising:
    providing a scent score defining a sequence of scent dispersion instructions arranged on a timeline;
    executing the sequence of scent dispersion instructions using one or more scent dispersion devices to produce multiple scents having intensity and composition that vary over time according to the scent score;
    distributing multiple scents produced by the one or more scent dispersion devices to a participant in the entertainment event, where each scent dispersion instruction of the sequence of scent dispersion instructions corresponds to at least one of the multiple scents and is distributed to the participant in time with a story element of a corresponding story script for the scripted entertainment event;
    providing a first scent media producing a first scent representing a first set of physical objects appearing in the entertainment event;
    providing a second scent media producing a second scent representing a second set of physical objects appearing in the entertainment event;
    wherein the entertainment event includes time-varying representations of the first and second sets of represented physical objects; and
    while displaying the entertainment event, controlling a quantity of scent molecules from one of the first scent media or the second scent media introduced into air surrounding the participant in coordination to a characteristic of the time-varying representations, wherein the characteristic includes a perceived distance between the participant and one of the respective first or second set of represented physical objects, a perceived size of one of the respective first or second set of represented physical objects, a perceived density of one of the respective first or second set of represented physical objects, a perceived atmospheric condition between the participant and one of the respective first or second set of represented physical objects, or perceived obstructions between the participant and one of the respective first or second set of represented physical objects;
    wherein controlling the quantity of scent molecules from the first scent media and controlling the quantity of scent molecules from the second scent media includes providing an amount of first scent molecules from the first scent media or an amount of second scent molecules from the second scent media by providing one or more of at least one pulse of the first scent molecules or at least one pulse of the second scent molecules to the air.

2. The method of claim 1, wherein distributing the multiple scents comprises distributing the multiple scents into a passenger area of an amusement park ride.

3. The method of claim 1, wherein distributing the multiple scents comprises distributing the multiple scents to a seating area of a theatre while displaying a film.

4. The method of claim 1, wherein the scent score timeline is coordinated with a timeline of at least one other sequentially delivered component of the scripted entertainment event, and the intensity and composition are defined by the scent score to create a representation of scents that would be generated by physical objects represented by the other sequentially delivered component.

5. A method of dispersing scents in congruity with entertainment, the method comprising:
    providing a first scent media producing a first scent representing a first set of physical objects appearing in the entertainment;
    providing a second scent media producing a second scent representing a second set of physical objects appearing in the entertainment;
    displaying the entertainment comprising time-varying representations of the first and second sets of represented physical objects; and
    while displaying the entertainment, controlling a quantity of scent molecules from one of the respective the first scent media or the second scent media introduced into air surrounding a participant in coordination to a characteristic of the time-varying representations, wherein the characteristic includes a perceived distance between the participant and one of the respective first or second set of represented physical objects, a perceived size of one of the respective first or second set of represented physical objects, a perceived density of one of the respective first or second set of represented physical objects, a perceived atmospheric conditions between the participant and one of the respective first or second set of represented physical objects, or perceived obstructions between the participant and one of the respective first or second set of represented physical objects
    wherein controlling the quantity of scent molecules from the first scent media and controlling the quantity of scent molecules from the second scent media includes providing an amount of first scent molecules from the first scent media and an amount of second scent molecules from the second scent media in relative proportions sufficient to create a perceivable scent evocatively associated with one or more of a story element, a plot line, a character, a location, a memory, an emotion, weather, time, or materials associated with the entertainment; and wherein controlling the quantity of scent molecules from the first scent media and controlling the quantity of scent molecules from the second scent media includes providing the amount of first scent molecules from the first scent media or the amount of second scent molecules from the second scent media by providing one or more of at least one pulse of the first scent molecules or at least one pulse of the second scent molecules to the air.

6. The method of claim 5, wherein controlling the quantity of scent molecules from the first and the second scent media includes mixing the amount of first scent molecules from the first scent media and the amount of second scent molecules from the second scent media in proportion to the perceived distance between the first and second sets of represented physical objects while a focus of the entertainment transitions between a represented first location and a represented second location.

7. The method of claim 6, wherein controlling the quantity of scent molecules from the first and the second scent media includes providing the amount of first scent molecules from the first scent media and the amount of second scent molecules from the second scent media in proportion to the focus of the entertainment on one or more of the respective first or second sets of physical objects present in the first location or the second location represented in the entertainment.

8. A method of dispersing scent in congruity with story-based entertainment, the method comprising:
providing a first scent media producing a first scent associated with a first story element, wherein the first scent represents a first set of physical objects appearing in the story-based entertainment;
providing a second scent media producing a second scent associated with a second story element, wherein the second scent represents a second set of physical objects appearing in the story-based entertainment;
wherein the story-based entertainment includes time-varying representations of the first and second sets of represented physical objects;
while displaying the story-based entertainment, controllably releasing the first and second scents in congruity with at least one of the first or second story elements; and
while displaying the story-based entertainment, controlling a quantity of scent molecules from one of the respective first scent media or the second scent media introduced into air surrounding a participant in coordination to a characteristic of the time-varying representations, wherein the characteristic includes a perceived distance between the participant and one of the respective first or second set of represented physical objects, a perceived size of one of the respective first or second set of represented physical objects, a perceived density of one of the respective first or second set of represented physical objects, a perceived atmospheric conditions between the participant and one of the respective first or second set of represented physical objects, or perceived obstructions between the participant and one of the respective first or second set of represented physical objects;
wherein controllably releasing the first and second scents includes controlling the quantity of scent molecules from the first scent media and controlling the quantity of scent molecules from the second scent media includes providing an amount of first scent molecules from the first scent media and an amount of second scent molecules from the second scent media in relative proportions sufficient to create a perceivable scent evocatively associated with one or more of the respective first or second story elements, a plot line, a character, a location, a memory, an emotion, weather, time, or materials associated with the entertainment; and
wherein controlling the quantity of scent molecules from the first scent media and controlling the quantity of scent molecules from the second scent media includes providing the amount of first scent molecules from the first scent media or the amount of second scent molecules from the second scent media by providing one or more of at least one pulse of the first scent molecules or at least one pulse of the second scent molecules to the air.

9. The method of claim 8, wherein the amount of one or more of the first or second scent molecules released is inversely related to an intended amount of evoked emotion of the correspondingly displayed story-based entertainment at a time of release of the first or second scents.

10. The method of claim 8, wherein the amount of one or more of the first or second scent molecules released is below a threshold amount consciously perceivable by the participant.

11. The method of claim 8, wherein the amount of one or more of the first or second scent molecules released is above a threshold amount consciously perceivable by the participant.

12. The method of claim 8, wherein while displaying the story-based entertainment, controllably releasing the first and second scents in congruity with at least one of the first or second story elements includes providing the first scent while displaying the first story element and providing the second scent while displaying the second story element to train the participant to associate the first and second scents with the first and second story elements during an initial part of the story-based entertainment.

13. A method of creating a time-varying scent experience, the method comprising:
displaying an entertainment experience in congruity with the time-varying scent experience;
dispersing a first scent from a first scent media in a perceivable magnitude into a breathing air volume of a participant during a first time period for a first duration, wherein the first scent represents a first set of physical objects appearing in the entertainment experience;
dispersing a second scent from a second scent media in a perceivable magnitude into the breathing air volume of the participant during a second time period for a second duration, wherein the second scent represents a second set of physical objects appearing in the entertainment experience;
wherein the entertainment experience includes time-varying representations of the first and second sets of represented physical objects;
reducing the perceivable magnitude of the first scent during a third time period for a third duration;

while displaying the entertainment experience, controlling a quantity of scent molecules from one of the respective first scent media or the second scent media introduced into air surrounding the participant in coordination to a characteristic of the time-varying representations, wherein the characteristic includes a perceived distance between the participant and one of the respective first or second set of represented physical objects, a perceived size of one of the respective first or the second set of represented physical objects, a perceived density of one of the respective first or the second set of represented physical objects, a perceived atmospheric conditions between the participant and one of the respective first or the second set of represented physical objects, or perceived obstructions between the participant and one of the respective first or the second set of represented physical objects;

wherein controlling the quantity of scent molecules from the first scent media and controlling the quantity of scent molecules from the second scent media includes providing an amount of first scent molecules from the first scent media and an amount of second scent molecules from the second scent media in relative proportions sufficient to create a perceivable scent evocatively associated with one or more of a story element, a plot line, a character, a location, a memory, an emotion, weather, time, or materials associated with the entertainment experience; and wherein controlling the quantity of scent molecules from the first scent media and controlling the quantity of scent molecules from the second scent media includes providing the amount of first scent molecules from the first scent media or the amount of the second scent molecules from the second scent media by providing one or more of at least one pulse of the first scent molecules or at least one pulse of the second scent molecules to the air.

14. The method of claim 13, wherein reducing the perceivable magnitude comprises evacuating the first scent from the breathing air volume.

15. The method of claim 13, wherein reducing the perceivable magnitude comprises introducing a neutralizing agent into the breathing air volume.

16. The method of claim 15, wherein introducing the neutralizing agent into the breathing air volume includes dispersing the neutralizing agent into the breathing air volume in an amount effective to render to the first scent consciously unperceivable to the participant.

17. The method of claim 13, wherein dispersing the first scent in the perceivable magnitude into the breathing air volume of the participant includes dispersing the first scent into the breathing air volume above a threshold amount subconsciously perceivable and below an amount that is consciously perceivable.

18. The method of claim 13, further comprising reducing the perceivable magnitude of the second scent during a fourth time period for a fourth duration.

* * * * *